United States Patent [19]

Amagase et al.

[11] Patent Number: 4,863,902

[45] Date of Patent: Sep. 5, 1989

[54] TREATMENT OF CANCER

[75] Inventors: Harunobu Amagase; Masato Arakawa; Ken Hashimoto, all of Hiroshima, Japan

[73] Assignee: Wakunaga Seiyaku Kabushiki Kaisha, Osaka, Japan

[21] Appl. No.: 935,740

[22] Filed: Nov. 28, 1986

[30] Foreign Application Priority Data

Nov. 28, 1985 [JP] Japan .............................. 60-268174
Nov. 28, 1985 [JP] Japan .............................. 60-268175
May 21, 1986 [JP] Japan .............................. 61-116557
May 21, 1986 [JP] Japan .............................. 61-116558

[51] Int. Cl.$^4$ ...................... A61K 37/02; A61K 43/00
[52] U.S. Cl. ........................................ 514/12; 514/2; 514/21; 424/1.1
[58] Field of Search ................... 514/17, 15, 802, 822, 514/12, 2, 21; 424/1.1

[56] References Cited

U.S. PATENT DOCUMENTS

| | | | |
|---|---|---|---|
| 4,619,913 | 10/1986 | Luck et al. | 514/802 |
| 4,652,441 | 3/1987 | Okada et al. | 514/822 |
| 4,659,696 | 4/1987 | Hirai et al. | 514/15 |
| 4,670,419 | 6/1987 | Uda et al. | 514/17 |

FOREIGN PATENT DOCUMENTS

| | | |
|---|---|---|
| 0162816 | of 0000 | European Pat. Off. |
| 86116559 | of 0000 | European Pat. Off. |
| 0161817 | 2/1985 | European Pat. Off. |

OTHER PUBLICATIONS

Biol. Abstr., vol. 78, (1984), 57077.
Chem. Abstr., vol. 104, (1986), 179637.
Chem. Abstr., vol. 106, (1987), 15608.
Chem. Abstr., vol. 72, (1970), 10101.
Biol. Abstr., vol. 82, (1986), 18869.
Biol. Abstr., vol. 82, (1986), 94532.
Biol. Abstr., vol. 81, (1986), 97302.
Biol. Abstr., vol. 78, (1984), 57080.
Chem. Abstr., vol. 105, (1986), 1303.
Journal of Biological Chemistry, (1984), vol. 259, pp. 7761-7766.
Cancer Letters, 28, (1985), 143-150, Elsevier Scientific Publishers Ireland Ltd., *Epidermal Growth Factor Stimulates the Growth of A431 Tumors in Athymic Mice*. Instruction 14, *Screening Data Summary Interpretation and Outline of Current Screen*, Drug Evaluation Branch, National Cancer Institute, Bethesda, Md., 20014.
Europ. J. Cancer, vol. 17, pp. 129-142, *Current Results of the Screening Program at the Division of Cancer Treatment*, National Cancer Institute, A. Goldin, et al.
P. 87, 2–Hormone Pharmacol., vol. 86, 1977, 134034.
11913, Chemical Abstracts, vol. 86, 1977, p. 32.
Cancer Treatment Reports, vol. 67, No. 9, Sep. 1983, The National Cancer Institute Antitumor Drug Discovery Program, Current and Future Perspectives: A Commentary, John M. Venditti.
The Journal of Biological Chemistry, vol. 258, No. 8, Issue of Apr. 25, pp. 5045–5049, 1983, Purification of Insulin Receptor with Full Binding Activity, Yoko Fujita-Yamaguchi et al.
Cell, vol. 40, pp. 747–758, Apr. 1985, The Human Insulin Receptor cDNA: The Structural Basis for Hormone-Activated Transmembrane Signalling.
Clinics in Endocrinology and Metabolism, vol. 13, No. 1, Mar. 1984, Somatomedin/Insulin-Like Growth Factor Tissue Receptors, S. Peter Nissley.
Cell, vol. 22, pp. 649–655, Dec. 1980, Serum-Free Cell Culture: A Unifying Approach by David Barnes and Gordon Sato.
Trans. Assoc. Am. Physicians, 85, 279–294, (1972); Reference No. 8; A Serotoninergic Mechanism for the Control of Insulin Secretion.

*Primary Examiner*—Delbert R. Phillips
*Attorney, Agent, or Firm*—Oblon, Spivak, McClelland, Maier & Neustadt

[57] ABSTRACT

Antitumor effect of antitumor agents or treatments is favorably controlled by a growth factor. The growth factor enhances antitumor actions of antitumor agents or treatments including those against which tumor or cancer has acquired resistant, or reduces side effects due to the antitumor agents or treatments. The most typical growth factors include human epidermal growth factor. A lot of tumors or cancers including human ones has been tested and a lot of growth factors has been tested, and the favorable control has been determined.

62 Claims, 8 Drawing Sheets

TREATMENT OF CANCER

BACKGROUND OF THE INVENTION

1. Technical Field

This invention relates to a novel antitumor agent and an antitumor action controlling agent. More particularly, the present invention relates to a novel antitumor agent comprising (a) a compound having antitumor action and (b) a growth factor, a peptide corresponding to a part of its constituent (fragment), a derivative of these or a salt of these (hereinafter sometimes called "growth factor, etc.") as the active ingredients, and also to a novel antitumor action controlling agent comprising a growth factor, a peptide corresponding to a part of its constituent (fragment), a derivative of these or a salt of these.

2. Prior Art

A growth factor is "a substance which promotes growth of animal cells in vivo or in vitro but is not a neutrient substance" [Ann. Rev. Biochem., 45, 531–558 (1976)], and, accordingly, hormones or carriers thereof known in the art also fall within the category of a growth factor.

At present, about 40 species of such factors have been known. Those growth factors may include, for example, those classified into the insulin family [insulin, insulin-like growth factors (IGF-I, IGF-II, etc.), mammary stimulating factor (MSF), nerve growth factor (NGF), etc.]; those classified into the epidermal growth factor family [epidermal growth factor (EGF), transforming growth factors ($TGF_\alpha$, $TGF_\beta$, $TGF_\gamma$, etc.]; those classified into the platelet-derived growth factor family [platelet-derived growth factor (PDGF), osteosarcoma-derived growth factor (ODGF), fibroblast growth factor (FGF), etc.]; and others [colony stimulating factor (CSF), T-cell growth factor, tumor angiogenesis factor (TAF), DNA synthesis promoting factor (DSF), tumor-derived growth factors, fibroblast-derived growth factor (FDGF), etc.]

Epidermal growth factor has been found in mammals. It can be isolated from human and horse urine, and also from rabbit, rat and mouse submaxillary glands. [Adv. Metab. Dis., 8, 265 (1975); and Japanese Laid-open Patent Publication No. 25112/1981]. Among them, human epidermal growth factor (hEGF) was isolated from human urine and introduced as the human-derived factor enhancing both proliferation and keratinization of epidermal tissue by S. Cohen in 1975 [Proc. Natl. Acad. Sci. USA, 72, 1317 (1975)], and it has been known that it is the same substance as the polypeptide reported as human urogastrone (h-UG) which inhibits gastric acid secretion and was isolated from human urine by H. Gregory et al., in the same year [Nature, 257, 235 (1975)]. Human epidermal growth factor/urogastrone has a molecular weight of about 6000, comprising 53 amino acid residues and having three disulfide bonds in its molecule [Metabolism (in Japanese), 17, 51–58 (1980)]. Epidermal growth factor is hereinafter referred to as EGF.

Physiological and pharmacological activities of EGF having been reported include inhibition of gastric acid secretion [Gut, 16, 1877 (1975); ibid, 23, 951 (1982)]; antiulcer action [Gut, 22, 927 (1981); Brit. J. Surg., 64, 830 (1977)]; protection of mucous membrane of digestive canal [Japanese Laid-open Patent Publication No. 9686/1985]; stimulation of DNA synthesis [Gut, 22, 927 (1981); J. Physiol., 325, 35 (1982)]; Enhancement of corneal epithelical regeneration [Exp. Eye Res. 14, 135 (1972)]; stimulation of bone resorption [Endocrinology, 107, 270 (1980)]acceleration of wound healing promoting action [Plast. Riconstr. Surg., 64, 766 (1979); J. Surg. Res., 33, 164 (1982)]; antiinflammatory activity (Japanese Laid-open Patent Publication No. 115784/1985); and analgesic activity (Japanese Laid-open Patent Publication No. 115785/1985), etc.

Some growth factors have been reported to be tumor promoter under limited conditions, in living bodies (hereinafter abbreviated as in vivo). For example, there is such a report on EGF which is one of the active ingredients in the present invention [Surgical Forum 16, 108 (1965); Experientia 32 (7), 913–915 (1976), Science 201, 515–518 (1978); Cancer Res. 39, 239–243 (1979)].

On the other hand, in test tubes, outside the living body (this is hereinafter abbreviated as in vitro), it has been well known that tumor cells having receptors for growth factors are rather inhibited in growth by addition of growth factors, and there is specifically a report that growth of tumor cells having EGF receptors is rather inhibited by addition of EGF [J. Biol. Chem., 259, 7761–7766 (1984); Toxicology Forum, in Japan, 9 (1), 55–62 (1986)]. Also, there is a report that cell growth, although not inhibited, is not enhanced at all by addition of EGF alone [Int. J. Cell Cloning, 3, 407–414 (1985)]. Generally speaking we cannot infer the physiological and pharmacological activities of growth factors in vivo from those in vitro.

Cancer is ranked as almost the first leading cause of death in a lot of countries today. Treatment of cancer is practiced in various ways. The treatment of cancer may include surgery, irradiation, chemotherapy, etc., the former two being local or non-systemic therapy. Since a local therapy can be applied with extreme difficulty when metastasis of the cancer has occurred to other portions than the original lesion, chemotherapy cannot but be relied upon. However, of the antitumor agents used in this method, those having strong antitumor effects have commonly strong adverse effects, and the chemotherapy method can be said to be limited in this respect.

Antitumor agents presently available may include alkylating agents (nitrogen mustard-N-oxide, triethylenemelamine, busulfane, carumustine, dacarbazine, etc.); antimetabolites [methotrexate, 6-mercaptopurine, 5-fluorouracil (5-FU), cytosine arabinoside (Ara-C), cyclocytidine, etc.]; antibiotics [adriamycin (Doxorubicine), actinomycin C, actinomycin D, chromomycin $A_3$, breomycin, etc.]; vinca alkaloids (vincrystine, demecolcine, etc.); prostaglandins; immunostimulators (polysaccharides such as Picibanil ®, Krestin ®, etc.); lymphocaines, monocaines (interferons, interleukine-2, etc.); platinum-complexes (cisplatin, etc.); and others.

Thus, there are a large number of antitumor agents which are presently clinically used, but among them specific antitumor agents tend to be used selectively for tumors of specific organs. At present, cancers which can be give 5-year survival by chemotherapy are infantile accute leukemia, Hodgikin's disease, orchioncus, Ewing's tumor, Wilm's tumor, Burkitt's lymphoma, papilloma, and otherwise embryonal rhabdomyosarcomas, skin cancer, ovarian tumor, breast cancer, multiple myeloma, neuroblastoma, etc. However, most of these cancers are relatively rare cancers, and it can be said that no satisfactory antitumor agent has been developed yet against stomach cancer, lung cancer (excluding some species thereof), liver cancer, esophagus cancer, colon cancer, etc., which will more frequently occur (textbook "Tumorology" in Japanese P. 269 (1984), published by Nanzando).

On the other hand, antimetabolites involve a problem different from the above problem. For example, 5-fluorouracil [A Comprehensive Treatise, 5, 327, Prenum Press, Cancer Res., 18, 478 (1958), Gastroenterlogy, 48, 430 (1965), Cancer Treat, Rep., 62, 533 (1987)] which is at present clinically frequently used is one of the antitumor agents having the strongest antitumor action, but it has been reported to have advese effects on digestive truct mucosa, bone marrow, etc. where mitosis of cells occurs abundantly to cause diarrhea or decrease in white blood cells, etc. [Pharmacological Principles of Cancer Treatment, 195 (1982)], and also other antitumor agents as mentioned above are also known to have various adverse effects [textbook "Illustrated Pharmacology", P. 384–385, Asakura Shoten, (1979)]. Thus, antitumor agents of the prior art having strong antitumor actions are generally also strong in their adverse effects. On the other hand, although 1-(2-tetrahydrofulyl)-5-fluorouracil (Tegafur) has relatively little toxicity and side effect, it is said to be slightly inferior in antitumor effect. Thus, those having little side effect are generally weak in their antitumor effects.

Also, a large number of therapies have been practiced for the purpose of potentiating the antitumor effect and preventing the adverse effects by combined use of multiple antitumor agents known in the art. However, no decisive therapeutical method has yet been established.

Further, as a difficulty, when continuous administration of an antitumor agent is practiced, there may sometimes occur a phenomenonthat the tumors acquire resistance to the antitumor agent, whereby the antitumor effect can be obtained with difficulty, This is a problem which is clinically extremely serious and is abruptly increasing in these days. The multiple-agent combined use therapeutical method is an attempt to overcome drug resistance by use of many kinds of antitumor agents with different mechanisms, but it cannot be said that resistance has been overcome, and further toxicity becomes by far heavier than when a single agent is employed.

Further, as to radiation therapy, methods have been developed for improvement of therapeutical results as a part of cancer therapy. Such methods include, for example, a method in which physical dose distribution is improved by irradiation of accelerated heavy ion particles or by a means using $\pi$ neutrons. However, according to the above method, the accelerator or auxiliary installations, etc., necessary for practicing the method are expensive and also many skilled engineers or physicians are required. Further, radiation therapy is also accompanied with the drawbacks such as great damage to normal tissues, etc.

Accordingly, in order to solve such problems, it has been desired to provide an antitumor agent having strong antitumor action and yet little side effect or an agent controlling antitumor action, and an effective application method of chemotherapy or other cancer therapeutical methods.

SUMMARY OF THE INVENTION

An object of the present invention is to solve the above problems, and as a result of intensive studies, growth factors, etc., were found to potentiate the antitumor action of a compound having antitumor action, and further exhibit antitumor effect inherent in the compound even against tumors resistant to the antitumor agents and yet prevent the adverse effect of the compound. On the basis of this knowledge, a novel antitumor agent and an antitumor action controlling agent have been completed, and it is intended to accomplish the above object by providing these.

Accordingly, the antitumor agent according to the present invention comprises (a) a compound having antitumor action, and (b) a growth factor, a peptide corresponding to a part of its constituent, a derivative of these or a salt of these as the active ingredients.

Also, the antitumor action controlling agent comprises a growth factor, a peptide corresponding to a part of its constituents, a derivative of these or a salt of these as the active ingredient.

The antitumor agent and the antitumor action controlling agent each comprises the above ingredients as the active ingredients, to solve the above problems, the former having the advantage of strong antitumor effect and little side effect, while the latter having the advantage of potentiating the antitumor effect of a compound having antitumor action and preventing its adverse effect.

Those which have hitherto been used as antitumor agents or known as compounds having antitumor action had various side effects as described above. However, the present invention has been accomplished on confirmation that further addition of a growth factor, etc., to a compound having antitumor action as mentioned above results in potentiating antitumor action of the above compound, exhibiting also the antitumor effect inherent in the compound even against tumors resistant to the antitumor agent and also inhibiting the side effect of the compound, as described previously.

Accordingly, the antitumor agent and the antitumor action controlling agent will be useful in therapy of cancer, particularly chemotherapy.

Also, it will be beneficial to use the medicament of the present invention for the purpose of enhancing the therapeutical effect of other cancer treatments such as radiation therapy than chemotherapy or thermotherapy (see, for example, Japanese Laid-open Patent Publication No. 67518/1982).

Of the active ingredients of the drug of the present invention, the growth factor, etc., itself has physiological and pharmacological activity. For example, EGF which is one of growth factors has been known to have the therapeutical effect against peptic ulcer in oral or parenteral dosage form (Japanese Laid-open Patent Publication No. 180270/1984), protection of mucous membrane of digestive canal (Japanese Laid-open Patent Publication No. 9686/1985), acceleration of wound healing [Plast. Reconstr. Surg., 64 766 (1979) J. Surg. Res., 33 164 (1982)]). Therefore, since the growth factor, etc., has such various actions, a unique therapy could be expected for the drug of the present invention comprising this as one of the active ingredients.

DETAILED DESCRIPTION OF THE INVENTION

Figure 1:
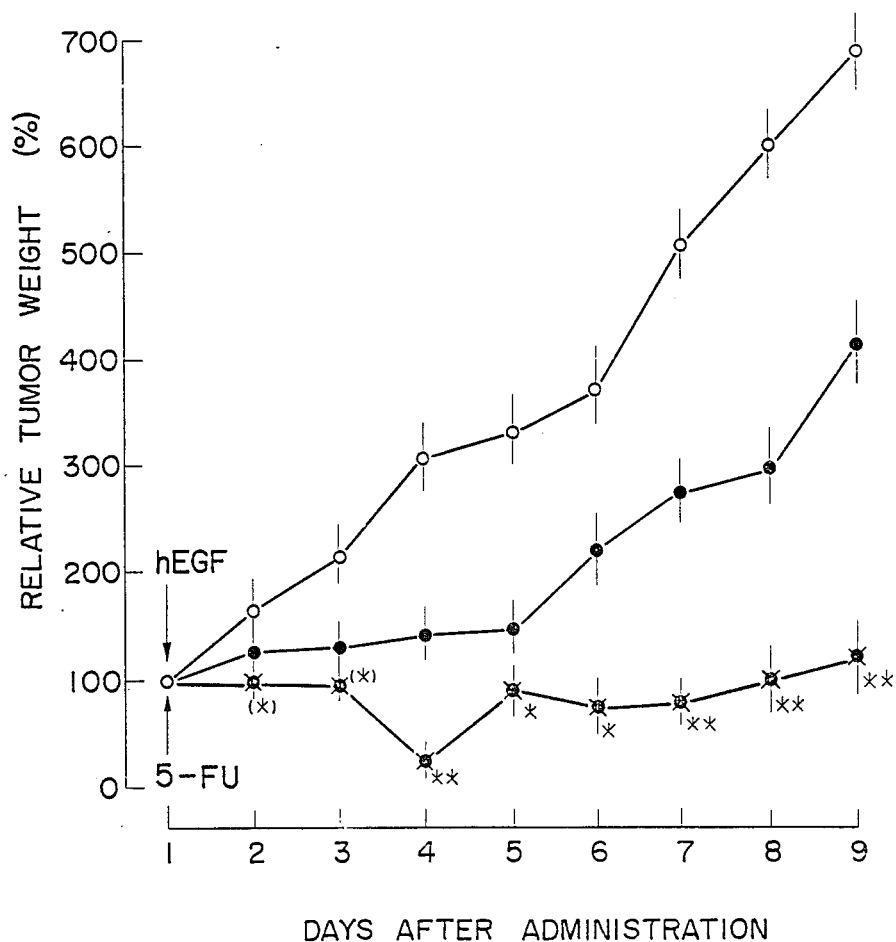
FIG. 1 is a graph showing the change with lapse of time of tumor weight in Experimental Example 1.

The antitumor agent of the present invention comprises the above components (a) and (b) as the active ingredients. The antitumor action controlling agent comprises only the component (b) as the active ingredient.

Compound having antitumor action (component (a))

The "compound having antitumor action" as mentioned in the present invention refers to a compound which can be used primarily for therapy of cancer, including medicaments used as the antitumor agents or anti-malignant-tumor agents, or compounds having antitumor action or anti-malignant-tumor action. Accordingly, any compound is included so long as it has anti-tumor action as the property inherently possessed by the compound, and examples of the compounds confirmed already to have such action include those as set forth below.

1. Alkylating agent

For example, there may be included chloromethyne analogues, nitrogen mustard analogues, ethyleneiminoanalogues, alkylsulfonic acid analogues, nitrosourea analogues, epoxide analogues, etc. [textbook "Chemotherapy of Cancer" p. 10–33 (1985), published by Nankodo]. Here, in the present invention "analogues" is the concept having the common skeletal structure with these compounds, capable of having activity, including derivatives subjected to any desired substitution or chemical modification and salts thereof. As such examples, nitrogen mustard analogues include yperite, nitrogen mustard N-oxide, cyclophosphamide (e.g. Japanese Laid-open Patent Publication No. 41892/1983, etc.), melphalan, chlorambucyl, uracil mustard, dopane, alanine-MN, etc. Examples of ethyleneimino analogues include triethylenemelamine, triethylenethiophosphoramide, carbazyl quinone, trenimone, etc. Nitrosourea analogues may be exemplified by carmustine, lomustine, etc.

2. Antimetabolites

For example, there may be included folic acid antagonist analogues (methotrexate, aminoputerine, etc.), purine antagonist analogues (6-mercaptopurine, 8-azaguanine, etc.), pyrimidine antagonist analogues [5-fluorouracil (see, for example, Japanese Laid-open Patent Publications Nos. 7231/1980, 65774/1976, 48677/1977, 42887/1977, 31676/1978)], 1-(2-tetrahydrofuryl)-5-fluorouracil (hereinafter referred to as Tegafur), Carmofur, etc.] and others [see the above textbook "Chemotherapy of Cancer" P. 33–52]. Also, a drug (UFT ®) having uracil formulated into Tegafur has been recently used clinically.

3. Antibiotics

For example, there may be included actinomycin analogues (actinomycin C, D, etc.), Azaserine, DON, Sarkomycin, Carzinophilin, Mitomycin analogues (e.g. Japanese Laid-open Unpatent Publication No. 67433/1985, etc.), Chromomycin $A_3$ analogues, Bleomycin (e.g. Japanese Laid-open Patent Publication No. 67425/1985, etc.), Peplomycin, Danurorubicin, Adriamycin (Doxorubicin) which is an anthracycline type antibiotic [e.g. Japanese Laid-open Patent Publication Nos. 178818/1985, 67425/1985, etc.], Aclarubicin, and others [see the above textbook "Chemotherapy of Cancer", P. 52–77].

4. Hormone agents

For example, there may be included sex hormone analogues (testosterone derivatives, estradiol derivatives, etc.), pituitary adrenocortical hormone analogues (cortisone, predonisone, dexametasone, etc.) and others [see the above textbook "Chemotherapy of Cancer", p. 77–88].

5. Vinca alkaloids

There may be included Demecolocin, Vinblastine, Vincristine, Podophyllotoxin and others [see the above textbook "Chemotherapy of Cancer", P. 89–97].

6. Porphyrin type substances

There may be included hematoporphyrin mercury complex, protoporphyrin.cobalt complex, etc. [see the above textbook "Chemotherapy of Cancer", P. 97].

7. Otherwise, there are immunostimulating agents [Krestin ® (PSK), Picibanil ®, Lentinan ®, etc.), platinum complexes [Cisplatin (e.g. Japanese Laid-open Patent Publication No. 152415/1981, etc.), Carboplatin, Ipuloplatin, etc.) [see "Chemotherapy of Cancer 1986" Recent Medicine 41 (3), extravolume P. 509–14 (1986), Saishin Igaku Co.], or otherwise lymphocaine, monocaine analogues (interferons, interleukins, etc.) [see the above textbook "Chemotheraphy of Cancer", P. 98–105].

Growth factors, etc. (component (b))

In the present invention, the "growth factor" refers to substance which can promote growth of animal cells in vivo or in vitro and is not a nutrient substance, and the hormones and carriers thereof of the prior art also fall within the category of growth factor as mentioned above.

Among the growth factors, as mentioned above, the epidermal growth factor family, the insulin family, the platelet-derived growth factor family, etc., may be included, all of which are available in the present invention. Typical of these are those of the epidermal growth factor family, such as the epidermal cell growth factor (ECF) and transforming growth factors (TGFs) as well as the insulin family such as insulin and those of the platelet-derived growth factor family such as fibroblast growth factor.

The present invention is inclusive of not only the above growth factors themselves which are naturally occurring, but also those which are different from the above factors in optional substitution of amino acids constituting those growth factors, amino acid addition or deficiency, etc., but have the same or similar physiological activities and pharmacological activities as said growth factors, so called fragments or derivatives.

Here, the amino acids which can be optionally substituted as the derivative may be any amino acid, provided that it can have the activity of a growth factor, and the amino acid to be substituted may be either that of a natural product or a derivative [analogue (e.g. one having fluorescence, or one having high lipid solubility, etc.)].

Further, the derivative of said growth factor is also inclusive of the derivatives of fragment. The fragment means to contain a portion having at least the binding activity with the growth factor receptor, having the partial structure of a part of said growth factor. For example, there may be included those in which one or more amino acids are lacking from the C-terminal or N-terminal, or those which are formed by cleavage at the C-terminal, N-terminal and any portion, comprising two or more amino acid. Also, of the above factors and derivatives thereof as described above, those which have not lost the terminal amino group and carboxyl group by chemical modification have free amino group and carboxyl group and therefore they can be salts with acids and salts with bases. As the acid and base to form such salts, it is generally possible to use organic or inorganic acids and bases acceptable in preparation of pharmaceuticals, specifically, for example, hydrochloric acid, surfuric acid, acetic acid, malonic acid, succinic acid, sodium hydroxide, amines, etc. The derivatives are inclusive also of those applied with various chemical modifications. Such derivatives can be obtained by, for example, chemical modification known per se such as alkylation, oxidation, reduction, hydrolysis, etc., or a chemical modification according to a combination of these.

Accordingly, the present invention is inclusive of not only the above growth factors themselves, but also peptides (fragment) having the partial structures of a part thereof, their derivatives and their salts. These growth factors, etc., can be prepared according to any desired method such as extraction from living bodies (specifically, blood, saliva, urine, tear fluid, mother milk, various tissues, organs, etc.) [growth factors and their derivatives, etc., can be prepared by various methods (see the literatures listed in "Cell Growth Factor" edited by Society of Tissue Culture of Japan, published by Asakura Shoten, 1984)], chemical synthesis or genetic engineering synthetic method, etc. And, the growth factors, etc., thus prepared should preferably be of high purity. As such a growth factor, there is epidermal growth factor. Epidermal cell growth factor can be isolated from urine of human or horse, and also from submandibular gland of rabbit, rat and mouse, and is known to exist in mammals regardless of its species [Adv. Metab. Dis-, 8, 265 (1975), Japanese Laid-open Patent Publication No. 25112/1981, etc.]. Among them, when the drug of the present invention is applied for human being, hEGF as mentioned above is preferred, and, for preparation of this EGF, there have been proposed, for example, the method to isolate it from living body components [Japanese Laid-open Patent Publications Nos. 99418/1983, 219124/1983, 204123/1984, Japanese Patent Publications Nos. 12744/1969, 4527/1978, 50315/1984, 50316/1984, 42650/1984], the chemical synthetic method [Japanese Laid-open Patent Publication No. 27858/1984] and the construction method according to the genetic engineering method [Japanese Laid-open Patent Publications Nos. 122096/1982, 216697/1983, 132892/1984].

And, the physiological and pharmacological activities of EGF which have been reported up to date include the action of inhibiting gastric acid secretion [Gut, 16, 1884 (1975), ibid, 23, 951 (1982)], antiulcer action [Gut, 22, 927 (1981), Brit. J. Surg., 69, 830 (1977)], the protection of digestive mucosa [Japanese Laid-open Patent Publication No. 9686/1985], stimulation of DNA synthesis [Gut, 22, 927 (1981), J. physiol., 325, 35 (1982)], stimulation of corneal would healing [Exp. Eye Res., 14, 135 (1972)], stimulation of bone resorption [Endocrinology, 107, 270 (1980)], stimulation of wound healing [Plast. Reconstr. Surg., 64, 766 (1979), J. Surge. Res., 33, 164 (1982)], antiinflammatory action (Japanese Laid-open Patent Publication No. 115784/1985) and analgesic action (Japanese Laid-open Patent Publication No. 115785/1985), etc., as mentioned above.

On the other hand, as an EGF derivative, there is proposed one constructed according to the genetic engineering method [which is prepared by substituting leucine for the 21st methyonine from the N-terminal of human EGF (hEGF) ([Leu$^{21}$]-hEGF; Japanese Laid-open Patent Publication No. 28994/1985)]. As another EGF derivative, hEGF-II lacking 2 amino acids from the C-terminal of hEGF has been also obtained [see Japanese Patent Application No. 22630/1985 proposed by the co-researchers of the present inventors; here, the hEGF prepared by genetic engineering by the co-researchers of the present inventors has high purity (about 99.9% or higher) and such a high purity is preferred for the component (b)]. Further, as other EGF fragments, there have been also known des-(49–53)-EGF(EGF-5), des-(48–53)-EGF(EGF-6) which are lacking 5 or 6 amino acids from the C-terminal of EGF [Biochemistry, 15, 2624 (1976), Mol. Pharmacol., 17, 314 (1980), Vitam. Horm., 37, 69 (1979), Clin. Res., 25, 312A (1977)], EGF-(20–31) which is considered to be the minimum unit for EGF to express various actions thereof or its derivative [(Acm)Cys$^{20,31}$] EGF-(20–31) [Proc. Natl. Acad. Sci., 81, 1351 (1984) or [Ala$^{20}$] EGF-(14–31) [Proc. Natl. Acad. Sci., 81, 1351 (1984)], CNBr-EGF which is a derivative obtained by treatment with cyanogen bromide [Biochemistry, 15, 2624 (1976)], etc., and such substances can be also the active ingredient of the drug of the present invention.

As one group of the growth factors, there is the epidermal growth factor family, and one example thereof is EGF as described above and transforming growth factor (TGF) as mentioned above.

And the TGF has a great portion similar in amino acid sequence to EGF, and is presently classified into the three classes. That is, they are TGF$_\alpha$, TGF$_\beta$ and TGF$_\gamma$. TGF$_\beta$, through synergetic action with TGF$_\alpha$ or EGF, promotes growth of cells. TGF$_\gamma$ exhibits singly such an action. EGF and the three kinds of TGF belong to the same category of growth factor family, particularly TGF$_{60}$ is highly similar in amino acid sequence to EGF, and 21 residues of the 50 residues of TGF$_{60}$ found at the homologous positions in EGF [Proc. Natl. Acad. Sci., 81, 7363 (1984)]. Also, TFG$_\alpha$ binds with EGF receptor, thus competing with EGF ["Igaku no Ayumi" 133, 1040–1044 (1985)]. Further, TGF$_\alpha$ activates EGF receptor kinase [Nature, 292, 259 (1981)], and anti-EGF receptor antibody cancer (MX-1), drug-resistant cancer was transplanted into experimental animal mouse, and the inhibiting effect of tumor cell growth when the active ingredients of the drug of the present invention are administered is examined, whereby the above action is confirmed.

Also, the effect of inhibiting or preventing the side effect of the above drug can be confirmed by body weight reduction of the experimental animal to which the tumor cells are transplanted. As to details about confirmation of these effects, reference should be made to the experimental examples shown below.

Antitumor agent

The antitumor agent of the present invention comprises the above "compound having antitumor action" (a) and the "growth factor, etc." (b) as the active ingredients. Thus, the antitumor agent of the present invention is different from the antitumor agent of the prior art. In the present invention, a growth factor, etc., is added as still another active ingredient to the compound having antitumor action.

The proportions of the above "compound having antitumor action" (a) and the "growth factor, etc." (b) formulated in the preparation of the present invention may be determined appropriately depending on the respective kind of the compound having antitumor action, since the antitumor action differs depending on the kind of the compound. For example, when (a) is 5-FU or Tegafur, and (b) is EGF, it is preferred that (a) should be used in an amount excessive over (b), about $10^2$ to $10^8$ moles, more preferably $10^4$ to $10^6$ moles of (a) relative to 1 mole of (b). When (a) is adriamycin or mitomycin C or cisplatin and (b) is EGF or insulin or $TGF\alpha$ or IGF-II, it is preferable to use about 1 to $10^6$ moles, more preferably $10^4$ to $10^6$ moles of (a) relative to 1 mole of (b). When (a) is cyclophosphamide and (b) is EGF or insulin or $TGF\alpha$ or IGF-II, it is preferable to use $5\times 10^1$ to $5\times 10^7$ mols, more preferably $5\times 10^3$ to $5\times 10^5$ stops the paracrine action of TGF [J. Biol. Chem., 259, 11895 (1984)]. From these results, EGF and $TGF_\alpha$ may be understood to have actions which are very approximate to each other. Also, similarly, insulin and IGF analogues have been reported to have similar actions as in the relationship between $TGF_\alpha$ and EGF [ADV. Metab. Dis., 8, 203, 211, 237 (1975), Endocrinology, 107, 1451 (1980)]. And, IGF analogues have also growth factor activity other than the insulin-like activity. The present invention is also inclusive of the factors of the same family having such similar actions.

Antitumor effect

The effect of the present invention is that the growth factors, etc. potentiate the antitumor effect inherent in various compounds having antitumor action against a wide scope of cancers and also inhibits or prevents its side effect.

Among them, the potentiating effect of the antitumor action of the above compound can be confirmed with the growth inhibition of the tumor cell transplanted into a test animal as the index when the compound which has been used solely as the antitumor agent and the growth factor used in combination. This method was employed, because the antitumor effect observed in vitro may be weak or disappear entirely in vivo.

More specifically, there are a large number of such examples. Particularly, it has been reported that Hinokitiol suppressed growth of tumor cells in an in vitro experimental system, but exhibited no effect at all against tumors of mouse in vivo [J. Med. Chem., 27, 1749-53 (1984)]. Similar results are also observed sometimes in medicaments other than this, and the in vivo experimental system was employed for such reasons. In the present invention, as a specific example, mouse colon adenocarcinoma (colon adenocarcinoma 26) caused by N-methyl-N-nitrosourethane, and mouse colon adenocarcinoma (colon adenocarcinoma 38), and further human breast moles of (a) relative to 1 mole of (6). When (a) is 5-FU or Tegafur and (b) is FGF, it is preferable to use about $10^3$ to $10^9$ mols, more preferably $10^5$ to $10^7$ mols of (e) relative to 1 mole of (b). When (a) is 5-FU or Tegafur, and (b) is EGF and $TGF\beta$, it is preferable to use about $10^2$ to $10^8$ moles, more preferably $10^4$ to $10^6$ moles of (a) relative to 1 mole of EGF and 10 to 300 moles of $TGF\beta$. When (a) is UFT ® and (b) is EGF or insulin or $TGF\alpha$ or IGF-II, it is preferable to use about 10 to $10^7$ parts by weight, more preferably $10^3$ to $10^5$ parts by weight of (a) relative to 1 part by weight of (b).

The active ingredients (a) and (b) of the present invention may be formed into preparations of various unit dosage forms singly respectively and administered separately, or alternatively both components may be previously formulated into a combined preparation and administered in various unit dosage forms.

Examples in which (b) is formed singly into a preparation as described above are shown in Examples 1–4, 23–26, 31, and 34–36.

Further, as the timing for administration, it can be selected adequately depending on the combination of the active ingredients (a) and (b) formed into preparations, and the latter may be administered simultaneously with administration of the former, or before or after administration of the former. In an embodiment of the present invention, in such a case as a combination of an antimetabolite, 5-FU and hEGF, it is preferable to administer hEGF (corresponding to the active ingredient (b)) before or during administration of 5-FU (namely corresponding to the active ingredient (a)). Also, as to the number of administration, it may be selected suitably depending on the form of the present drug or the active ingredient used, and further according to the symptoms, etc., of the patient. And, the antitumor agent according to the present invention ordinarily comprises the above active ingredients and auxiliary components in preparation. Of these, specific examples of auxiliary components may include carriers (excipients, binders, diluents, etc.), stabilizers, preservatives, dissolving aids, etc. Examples of the carrier include calcium carbonate, lactose, sucrose, sorbitol, mannitol, starch, amylopectin, cellulose derivatives, gelatin, cacao fat, water, paraffin, oil and fat, etc. In the case of water, paraffin and oil and fat, this may act as a solvent or otherwise the antitumor agent of the present invention may be formed into an emulsion or a suspension.

As the dosage form for administration, various forms can be selected depending on the therapeutical purpose, including, for example, preparations for oral administration such as powder, granule, fine granule, tablet, pill, capsule, troach, etc.; preparations for parenteral administration such as suppository, lotion, injection (for example, the active ingredients of the present invention are dissolved or suspended in distilled water for injection or various infusions, etc.), ointment, poultice, etc.; or any other administrable form such as one applied with elaboration such as sustained release property, etc. These can be administered orally or parenterally (including injection), and moreover other drugs can be also formulated, if desired.

The dose may be determined depending on the age, body weight, severity of disease, etc., of the patient. for oral and parenteral (including injection) administration, a dose of about 10 ng to 10 mg as the growth factor, etc., for human adult per day is generally desirable. The dose of a compound having antitumor action is not required to set particularly a special condition, but it can be the known dose for each compound. For example, in the case of 5-FU and adriamycin, the injected dose per day is about 5 to 15 mg/Kg body weight and 10 to 20 mg/Kg body weight respectively. The dose by oral administration of 5-FU for human adult per day is 100 to 300 mg.

A desirable specific example of the present invention is in the unit dosage form for administration of the dose per day once or several times per day.

The antitumor agent according to the present invention is of low toxicity because there is no change in general symptoms even when the above polypeptide is administered at a dose of 10 mg/Kg by subcutaneous injection, at a dose of 1 mg/Kg by intravenous injection to male and female mice and rats (5 animals in each group) (corresponding to about 1000000-fold and about 500000-fold of the concentration in human blood, respectively) and at a dose of 5 mg/Kg by oral administration, and there is also no dead case.

The cancer to be treated by the antitumor agent of the present invention is determined depending on the growth factor, etc., and the compound having antitumor action respectively of the active ingredients in the drug of the present invention. Accordingly, the drug of the present invention can be prepared so as to be effective for all cancers by selecting suitably the active ingredient (a) and the active ingredient (b).

Antitumor action controlling agent

The antitumor action controlling agent of the present invention comprises the above component (b) as the active ingredient. And, the antitumor action controlling agent according to the present invention comprises ordinarily the above active ingredient and auxiliary components in preparation. In short, it can be formed into a preparation suitably following the method as disclosed for the above antitumor agent.

When the agent of the present invention is used for the purpose of potentiating the therapeutical effect of chemotherapy by combined use of a compound having antitumor action and the agent of the present invention, it is administered simultaneously with administration of the compound having antitumor action or before or after administration thereof. As the compound having antitumor action of which effect is to be potentiated with the agent of the present invention, those as mentioned above may be exemplified.

When the agent of the present invention is used as the radiation sensitizer for the purpose of enhancing the therapeutical effect of radiation therapy, it may be added before or after irradiation of radiation in radiation therapy, or during irradiation if the situation permits it. Concerning radiation therapy itself, it is not required to employ particularly a special method or conditions, but radiation therapy techniques in general may be applied as such. By use of the agent of the present invention in combination, radiation therapy is possible in the lower dose region as compared with the prior art.

As the source for radiation irradiation, general sources such as X-ray linac high energy X-ray, betatron 32 MeV electron ray, $^{60}$Co-ray, etc.

Also, when the agent of the present invention is used as the thermal sensitizer for the purpose of enhancing the therapeutical effect of thermotherapy, the same administration method as in radiation therapy may be used. In the thermotherapeutical method by use of the present agent in combination, no special method, conditions, etc., are required to be employed, but thermotherapeutical techniques may be applied as such.

EXPERIMENTAL EXAMPLES

In these experimental examples, when the active ingredient (a) and the active ingredient (b) are administered in combination, as shown in Reference Example 2, the same effects were obtained in both the cases when administered by individual injections (separate injection) and when administered by injection of a mixture of these components (mixed injection), and therefore the results by administration of a combination of these components are those of separate injection, unless otherwise specifically noted.

Experimental Example 1

Antitumor effect was examined by combination of 5-FU and hEGF which are antimetabolites.

(1) Experimental animals

After BALB/c mice were preliminarily fed in a thermostat (23°±0.5° C.), humidistat (60±5%) room for 1 week, those which appear to be healthy weighing 18–20 g were provided for the present experiment in 6–12 mice per 1 group.

(2) Experimental method and results

Colon adenocarcinoma 26 (mouse colon adenocarcinoma) was minced into pieces and about 0.1 to 0.2 ml thereof was transplanted subcutaneously on the right side of mouse abdomen by a cell transplanting needle (trocker). Six days after transplantation, the size of tumor, namely longer diameter (a mm) and shorter diameter (b mm) of tumor were measured and the tumor weight was calculated according to the formula shown below [Instruction 14 (NCI) 1980].

$$\text{Tumor weight (mg)} = ab^2/2$$

[Since the tumor phyma takes generally a shape of a spheroid, the formula for calculation of the volume of spheroid was introduced. Also, with the specific gravity of tumor cell as being about 1, volume was made equal to weight].

Before carrying out experiments, tumor weights were measured immediately before administration of the compounds and the mice were grouped into 3 groups by use of random numbers so that there may be no difference in average value of the tumor weights on initiation of experiments between the respective groups to make even the average values of tumor weights of the respective groups, and thereafter the compounds were administered to the respective groups.

First, in order to see the antitumor action potentiating effect by the present invention, in the group to which 150 mg/Kg of 5-FU which has been frequently used as a compound having antitumor action was alone subcutaneously administered, in the group to which 150 mg/Kg of 5-FU and 100 μg/Kg of human EGF (hEGF) were subcutaneously administered in combination and in the group to which no compound was administered, the weight change with lapse of time of the transplanted tumor cell was measured. The results are as shown in FIG. 1. In this FIGURE, the axis of abscissa indicates the experimental days with the day of compound administration being the day 1, and the axis of ordinate indicates tumor cell growth ratio which is the ratio of the tumor weight after elapse of the respective days relative to the tumor weight on the day 1 as being 100%.

Also, the respective symbols in the FIGURE have the following meanings.

5-FU:
5-FU administration (subcutaneous)
hEGF:
hEGF administration (subcutaneous)
:
hEGF+5-FU combined administration group
:
5-FU administration group
:
no compound administration group
**:
$P<0.01$
*:
$P<0.05$
(*):
$P<0.1$

[P indicates the risk rate when considering the statistical significance relative to the 5-FU single administration group, and all of these values are obtained according to Student's t-test or Aspin-Welchi method].

The test solutions employed are as shown below.
hEGF:
a solution of hEGF dissolved in a solvent (physiological saline containing 0.01% Tween 80) to 100 μg/10 ml/Kg.
5-FU:
a solution of 5-FU dissolved in a solvent (physiological saline containing 10% dimethyl sulfoxide) to 150 mg/10 ml/Kg.

To the control group (no compound administration group), both of the solvents for the above hEGF and 5-FU were administered.

As the result, in the group to which 5-FU and hEGF were administered in combination, tumor cell growth inhibiting effect could be seen not only as compared with the no compound administration group but also so compared with the 5-FU single administration group. Thus, the antitumor effect of 5-FU was found to be remarkably potentiated.

Experimental Example 2

By use of adriamycin which is an antibiotic type antitumor agent, the antitumor action potentiating effect was examined similarly as the above Experiment 1.

Experimental method and results

The experiment was conducted in the same manner as in Experimental Example 1.

However, the test solution administration groups were made a group to which 10 mg/Kg of adriamycin was administered singly subcutaneously, the group to which 10 mg/Kg of adriamycin and 100 μg/Kg of hEGF were administered in combination subcutaneously and the group to which no compound was administered.

Figure 2:
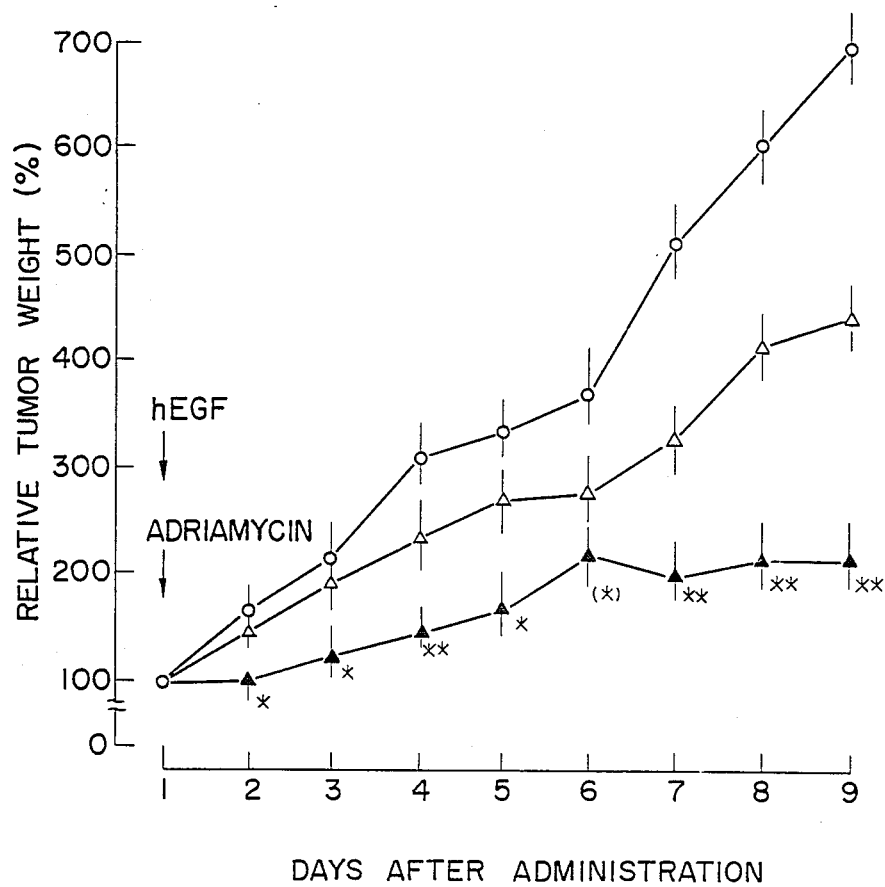
FIG. 2 is a graph showing the change with lapse of time of tumor weight in Experimental Example 2.

The results obtained were as shown in FIG. 2. The symbols in the FIGURE have the following meanings.
▲:
hEGF+adriamycin combined administration group
△:
adriamycin administration group, others are the same as above.

The test solutions were as follows.
hEGF: the same as in Experimental Example 1.
Adriamycin: used as a solution by adding physiological saline to Adriacin ® [produced by Kyowa Hakko Kogyo K. K.] to 10 mg/10 ml/Kg.

From these results, a remarkable tumor growth inhibiting effect was recognized on the next day after administration by combined use of 10 mg/Kg of adriamycin and 100 μg/Kg of hEGF, and the tumor cell became a size of about one third of that of the adriamycin single administration group to the day 9 after administration, thus indicating statistically significant persistent antitumor action potentiating effect.

Experimental Example 3

Next, by use of insulin among the growth factors, etc., antitumor action potentiating effect was examined similarly as in the foregoing Experimental Example 1.

Experimental method and results

The experiment was conducted in the same manner as in Experimental Example 1.

However, the test solution administration groups were made a group to which 150 mg/Kg of 5-FU was administered singly subcutaneously, a group to which 150 mg/Kg of 5-FU and 50 μg/Kg of insulin were administered in combination subcutaneously, a group to which 50 μg/Kg of insulin was administered singly subcutaneously and a group to which no compound was administered.

Figure 3:
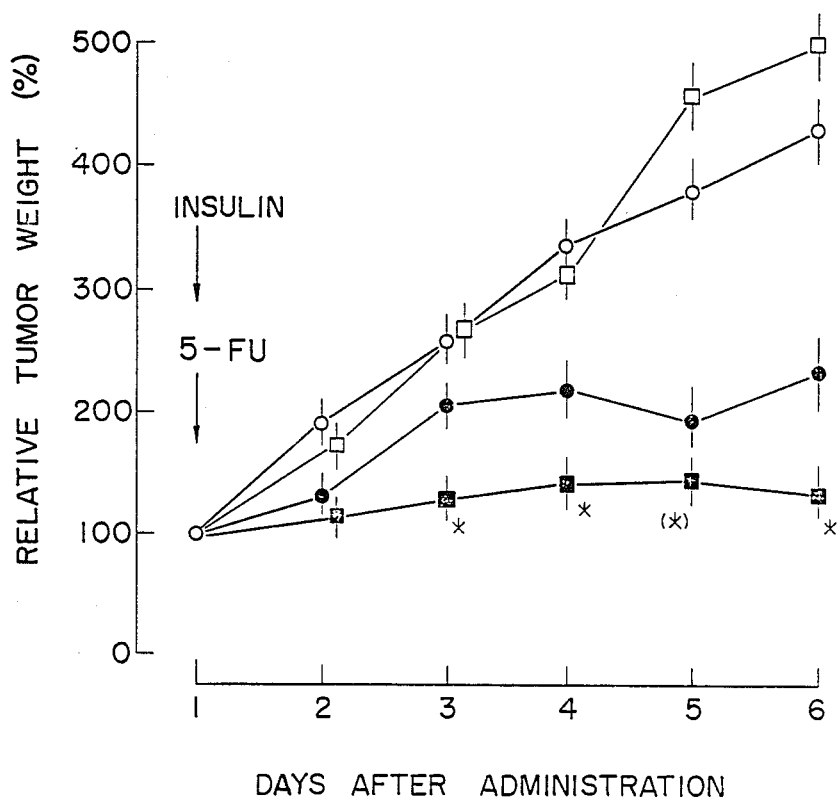
FIG. 3 is a graph showing the change with lapse of time of tumor weight in Experimental Example 3.

The results obtained were as shown in FIG. 3. The symbols in the FIGURE have the following meanings.
○:
no compound administration group
●:
5-FU administration group
■:
insulin+5-FU combined administration group
□:
insulin administration group The test solutions were as follows.
Insulin:
a solution of insulin dissolved in a solvent (physiological saline containing 0.005N hydrochloric acid) to 50 μg/10 mg/Kg
5-FU:
the same as in Experimental Example 1.

From these results, a remarkable tumor growth inhibiting effect could be recognized on the next day after administration by combined use of 50 μg/Kg of insulin and 150 mg/Kg of 50-FU, and the size of tumor was suppressed to the same extent as on the administration day to the day 6 after administration. As compared with the 5-FU single administration group, the size was about half, in the Figure, as attached with the marks of (*), *, a statistically significant persistent potentiating action of antitumor effect as compared with 5-FU single administration group was recognized.

Experimental Example 4

(1) Experimental animals

After C57BL/6 strain male mice were preliminarily fed in a thermostat (23±0.5° C.), humidistat (60±5%) room for 1 week, those which appear to be healthy weighing 18–20 g were provided for the present experiment in 10–20 mice per 1 group.

(2) Experimental method and results

Colon adenocarcinoma 38 (mouse colon adenocarcinoma) was minced into pieces and about 0.1 to 0.2 ml thereof was transplanted subcutaneously on the right side of mouse abdomen by a cell transplanting needle (trocker). Eleven days after transplantation, the size of tumor, namely longer diameter (a mm) and shorter diameter (b mm) of tumor were measured and the tumor weight was calculated according to the formula shown below [Instruction 14 (NCI) 1980].

Tumor weight (mg) = $ab^2/2$

[Since the tumor phyma takes generally a shape of a spheroid, the formula for calculation of the volume of spheroid was introduced. Also, with the specific gravity of tumor cell as being about 1, volume was made equal to weight].

Before carrying ot experiments, tumor weights were measured immediately before administration of the compounds (on the day 11 after tumor transplantation) and the mice were grouped into 3 groups by use of random numbers so that there may be no difference in average value of the tumor weights on initiation of experiments betwen the respective groups to make even the average values of tumor weights of the respective groups, and thereafter the compounds were administered to the respective groups.

In order to see th antitumor action potentiating effect of the growth factor by the present invention, the above experiments were carried out in a group to which 150 mg/Kg of 5-FU which has been frequently used as a compound having antitumor action was administered singly subcutaneously, a group to which 150 mg/g of 5-FU and 100 μg/Kg of hEGF were administered in combination subcutaneously and a group to which no compound was administered. The results were as shown in Table 1.

In the Table, days indicate the experimental days with the day of compound administration being as the day 1, and the tumor weight immediately before administration of compound of day 1 is made 100. The respective values show the average value ± standard error of case numbers of 10 to 20, in the Table, the marks of (*), * and *** indicate the statistical significance difference of the combined administration group relative to the 5-FU single administration group (the definition of P is as defined above).

From these results, in the hEGF+5-FU combined administration group, significant tumor cell growth inhibition was recognized relative to the 5-FU single administration group on the day 3 after administration and thereafter. Also, by use of [Leu²¹]-hEGF or hEGF-II in place of hEGF, the same experiment as above was conducted to obtain the same results.

TABLE 1

| Days | No compound administration group | 5-FU single administration group | hEGF/5-FU combined administration group |
|---|---|---|---|
| 1 | 100 | 100 | 100 |
| 2 | 194.9 ± 58.1 | 106.3 ± 31.8 | 60.3 ± 10.3 |
| 3 | 239.8 ± 57.6 | 88.3 ± 5.6 | 39.3 ± 11.4** |
| 4 | 232.5 ± 15.5 | 84.5 ± 7.0 | 25.2 ± 5.5** |
| 5 | 313.6 ± 21.3 | 75.4 ± 10.3 | 42.0 ± 11.3* |
| 6 | 415.6 ± 24.2 | 86.2 ± 9.5 | 53.7 ± 15.3(*) |
| 7 | 524.5 ± 50.6 | 121.1 ± 13.0 | 59.0 ± 14.3** |
| 8 | 621.2 ± 62.0 | 147.3 ± 16.0 | 67.9 ± 14.9** |
| 9 | 706.0 ± 70.7 | 210.9 ± 22.9 | 76.5 ± 15.6** |

Experimental Example 5

In order to examine the effect of hEGF which is one of the growth factors, etc., to prevent the adverse effect of the compound having antitumor activity, the following measurement was conducted in Experimental Example 1.

Figure 4:
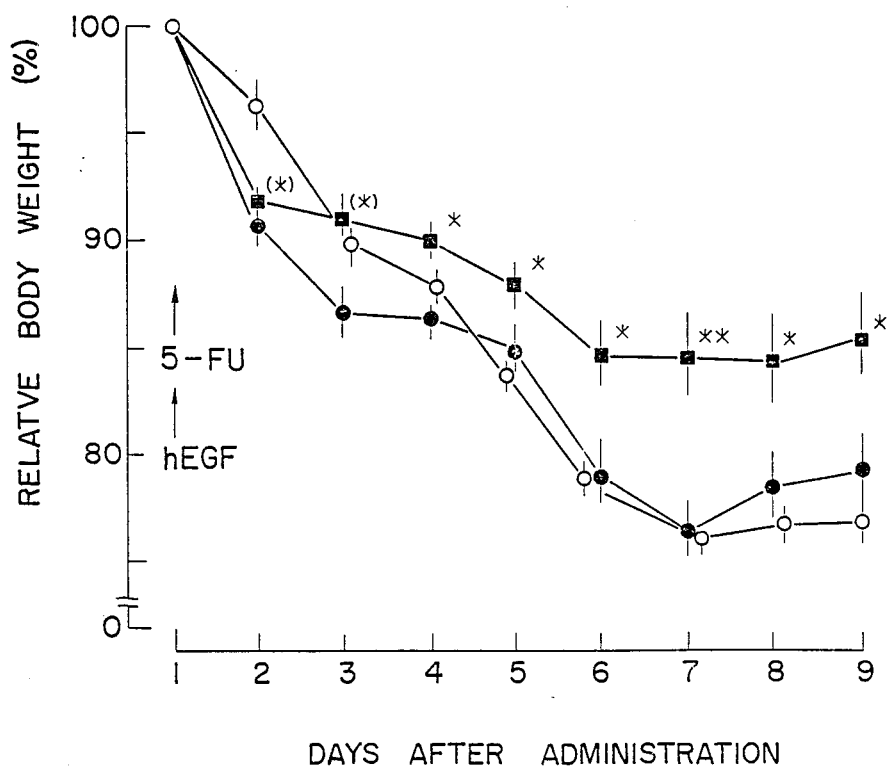
FIG. 4 is a graph showing the change with lapse of time in body weight of experimental animals.

That is, in Experimental Example 1, with the value of the body weight of the experimental animal immediately before administration of the drug from which the tumor weight is detracted as being 100, the ratio of the value of the total body weight of the experimental animal from which the tumor weight is detracted on the respective days after administration of the drug relative to this weight was calculated to obtain the results shown in FIG. 4. The symbols in the Figure are the same as in Experimental Example 1.

From these results, although no inhibiting effect of weight reduction could be recognized by single administration of 5-FU, but statistically significant body weight reduction inhibiting effect could be seen in the group by combined use of hEGF and 5-FU as compared with the no compound administration group or the 5-FU single administration group.

Experimental Example 6

By use of 5-FU which is an antimetabolite type antitumor agent, the antitumor effect by combined use of hEGF+5-FU against the solid tumor of mouse leukemia resistant to 5-FU was assayed by measurement of increase or decrease of tumor weight.

(1) Experimental animals

CDF$_1$ strain male mice were employed. The feeding conditions, etc., were the same as in Experimental Example 1.

(2) Experimental method and experimental results

Of P388 (mouse leukemia), the strain having chemical resistance to 5-FU (P388/5-FU) was previously grown in the abdomen of CDF$_1$ mouse. Eight days after transplantation into the abdomen, ascites (containing tumor cells) were collected, diluted with a liquid medium and transplanted subcutaneously at the axilla of mouse in $3 \times 10^6$ cells per mouse. Eight days after transplantation, the size of tumor was measured according to the same method as in Example 1 (Colon 26) and the tumor weight was calculated.

The grouping operation of mouse on initiation of experiments was conducted in the same manner as in Experimental Example 1. As for administration of compounds, the same procedure as in Experimental Example 1 was used. However, the administration was effected twice on the day 1 and the day 3.

The test solutions were as follows.
hEGF: the same as in Experimental Example 1.
5-FU: the same as in Experimental Example 1.
The results obtained were as shown in Table 2.

In the same Table, days indicate the experimental days with the day of compound administration being as the day 1, and the tumor weight immediately before administration of compound on the day 1 is made 100. The respective values indicate average value ± standard error of 9 mice. In the Table, the marks (*), * and ** indicate the statistical significance difference of the combined administration group relative to the 5-FU single administration group (definition of P is the same as above).

From these results, in the hEGF+5-FU combined administration group, significant tumor cell growth inhibition was recognized relative to 5-FU single administration group and the no compound administration group on the next day after administration.

Thus, from the fact that the effect was exhibited not only against adenocarcinoma but also against leukemia, it is readily conceivable that remarkable antitumor effect would be exhibited against many tumors.

Also, the mouse leukemia P388 used in this Experimental example has resistance to 5-FU and the antitumor effect recognized against this tumor suggests that an effective effect would be exhibited also against tumors which became resistant to drugs.

TABLE 2

| Days | Group without compound treatment | 5-FU single administration group | hEGF/5-FU combined administration group |
|---|---|---|---|
| 1 | 100 | 100 | 100 |
| 2 | 147 ± 15.1 | 126.2 ± 5.5 | 105.0 ± 6.6* |
| 3 | 227.9 ± 16.1 | 232.7 ± 15.9 | 154.1 ± 14.1** |
| 4 | 266.8 ± 32.6 | 280.0 ± 31.7 | 180.4 ± 23.2* |

Experimental Example 7

By use of [Leu$^{21}$]-hEGF which is a derivative of hEGF with the 21st methyonine (Met) from the N-terminal of amino acid sequence being substituted with leucine (Leu) and hEGF-II which is a fragment lacking two amino acid residues on the C-terminal side in the amino acid sequence of hEGF, the antitumor effect by combined use of [Leu$^{21}$]-hEGF and 5-FU and combined use of hEGF-II and 5-FU were assayed by measurement of change of tumor weight in the same experimental system as the above Experimental Example 6.

Although hEGF-II in a fragment of hEGF, its binding ability of receptor or biological activity is the same as hEGF [J. Biol. Chem., 247, 7659 (1972)].

The experiment was carried out in the same manner as in Experimental Example 6, except that the test solution administration groups were made a group to which 150 mg/Kg of 5-FU was administered singly subcutaneously, a group to which 150 mg/Kg of 5-FU and 100 μ/Kg of [Leu$^{21}$]-hEGF were administered in combination subcutaneously, a group to which 150 mg/Kg of 5-FU and 100 μg/Kg of hEGF-II were administered in combination subcutaneously and a group without treatment of compound.

The test solutions are as shown below.
[Leu$^{21}$]-hEGF:
  the same as hEGF in Experimental Example 1.
hEGF-II:
  the same as hEGF in Experimental Example 1.

The results obtained were as shown in Table 3. The symbols in the same Table are the same as explained for Table 2.

From these results, in the [Leu$^{21}$]-hEGF+5-FU combined administration group and the hEGF-II+5-FU combined administration group, a remarkable antitumor effect could be seen against the tumor resistant to 5-FU similarly as hEGF.

TABLE 3

| Days | Group without compound treatment | 5-FU single administration group | [Leu$^{21}$]-hEGF/5-FU combined administration group | hEGF-II/5-FU combined administration group |
|---|---|---|---|---|
| 1 | 100 | 100 | 100 | 100 |
| 2 | 147.4 ± 15.1 | 121.2 ± 10.5 | 92.0 ± 48* | 94.5 ± 5.1* |
| 3 | 227.9 ± 16.1 | 232.7 ± 15.9 | 108.3 ± 18.1** | 99.8 ± 4.8** |
| 4 | 268.8 ± 32.6 | 280.0 ± 31.7 | 160.4 ± 12.3** | 180.5 ± 20.4* |

Experimental Example 8

By use of cisplatin which is one of the antitumor platinum complexes, antitumor action potentiating effect was examined similarly as in Experimental Example 1.

The experiment was carried out as in Experimental Example 1 except that the test solution administration groups were made a group to which 5 mg/Kg of cisplatin was administered singly subcutaneously, a group to which 5 mg/Kg of cisplatin and 100 μg/Kg of hEGF were administered subcutaneously in combination and a group without treatment of compound.

Figure 5:
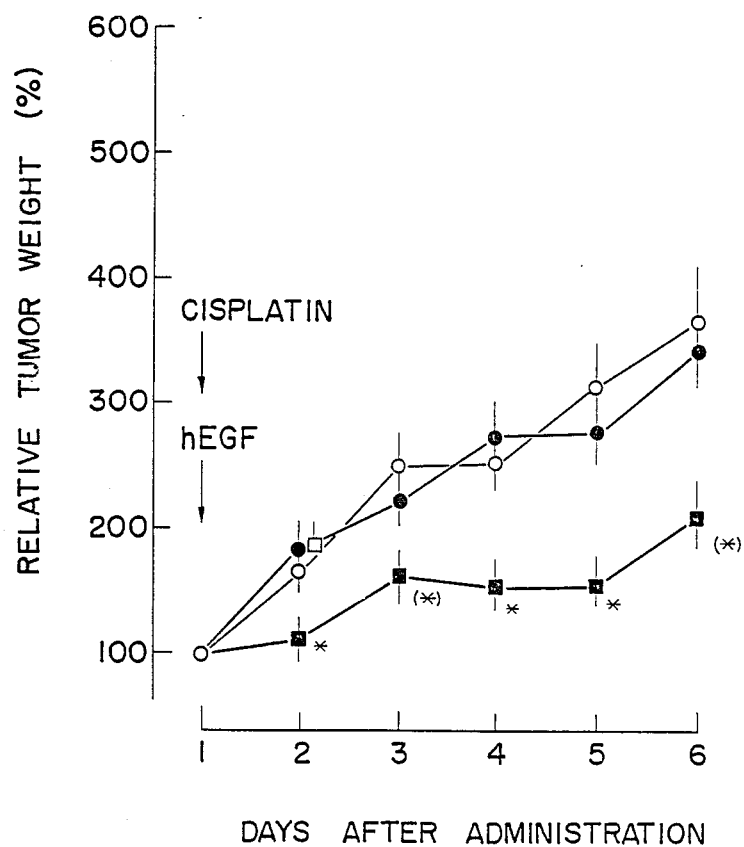
FIG. 5 is a graph showing the change with lapse of time of tumor weight relative to that immediately before administration of the compound (on the day 1) in Experimental Example 8.

The results obtained were as shown in FIG. 5. The symbols in the Figure have the following meanings:
  ●: cisplatin administration group
  ■: hEGF+cisplatin administration group, others are the same as described above.

The test solutions were as follows.
hEGF: the same as in Experimental Example 1.
Cisplatin: Randa ® (produced by Nippon Kayaku K.K.) was administered to 5 mg/10 ml/Kg.

From these results, by combined use of 5 mg/Kg of cisplatin and 100 μg/Kg of hEGF, a remarkable tumor growth inhibiting effect was recognized from the next day after administration, and the tumor phyma became about half of the size of the cisplatin single administration group and the no compound treatment group to the day 6 after administration. Thus, a statistically significant persistent antitumor action potentiating effect could be recognized.

Tumors of digestive organ system are generally non-sensitive to cisplatin. This experiment shows that digestive organ tumor inherently non-sensitive to cisplatin can be converted to cisplatin sensitive by hEGF.

When the same experiment was conducted by use of hEGF-II in place of hEGF, the same results were obtained.

Experimental Example 9

The antitumor action potentiating effect against mouse colon adenocarcinoma 38 was examined by combination of cisplatin which is a platinum preparation system antitumor agent and hEGF similarly as in Experimental Example 4.

The experimental method is the same as in Experimental Example 4 and the test administration groups are the same as in Experimental Example 8.

Figure 6:
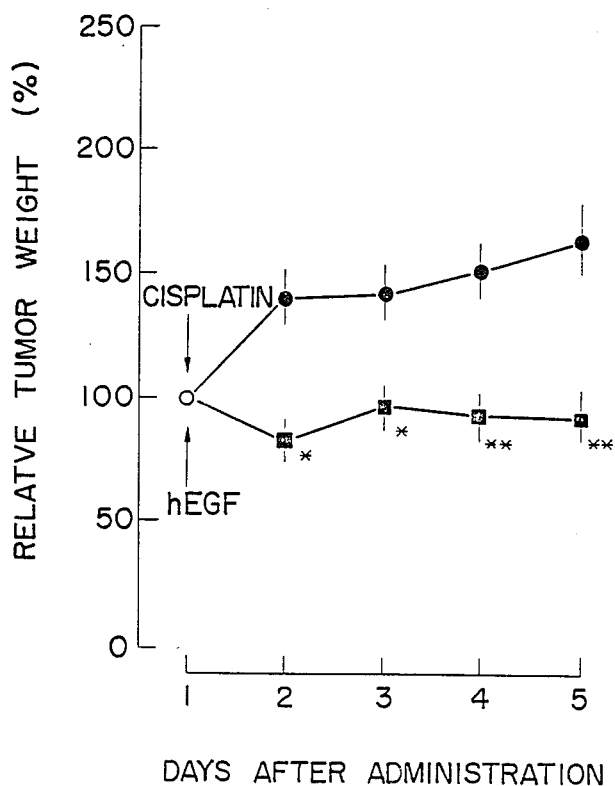
FIG. 6 is a graph showing the change with lapse of time of tumor weight relative to that immediately before administration of the compound (on the day 1) in Experimental Example 9.

The results obtained were as shown in FIG. 6. The symbols in the Figure and the test solutions are the same as in Experimental Example 8. From these results, a remarkable efect of combined use of hEGF could be recognized on the next day after administration not only against mouse colon adenocarcinoma 26 but also against mouse colon adenocarcinoma 38 which is slow in growth speed and more approximate to human tumor with respect to growth speed, and the size of the tumor phyma remained smaller than the size immediately before administration to the day 5 after administration, with its size being about ⅔ of the group to which cisplatin was administered singly. Thus, a statistically significant persistent antitumor action was recognized.

When the same experiment as above was conducted by use of [Leu$^{21}$]-hEGF in place of hEGF, the same results were obtained.

Experimental Example 10

By use of adriamycin which is an antibiotic system antitumor agent, the antitumor action potentiating effect of [Leu$^{21}$]-hEGF which is a derivative of hEGF was examined similarly in the above Experimental Example 2.

The experiment was carried out in the same manner as in Experimental Example 2 except that the test solution administration groups were made a group to which 10 mg/Kg of adriamycin was administered singly subcutaneously, further separately, a group to which 10 mg/Kg of adriamycin and 100 μg/Kg of [Leu$^{21}$]-hEGF were administered in combination subcutaneously and a group to which no compound was administered.

Figure 7:
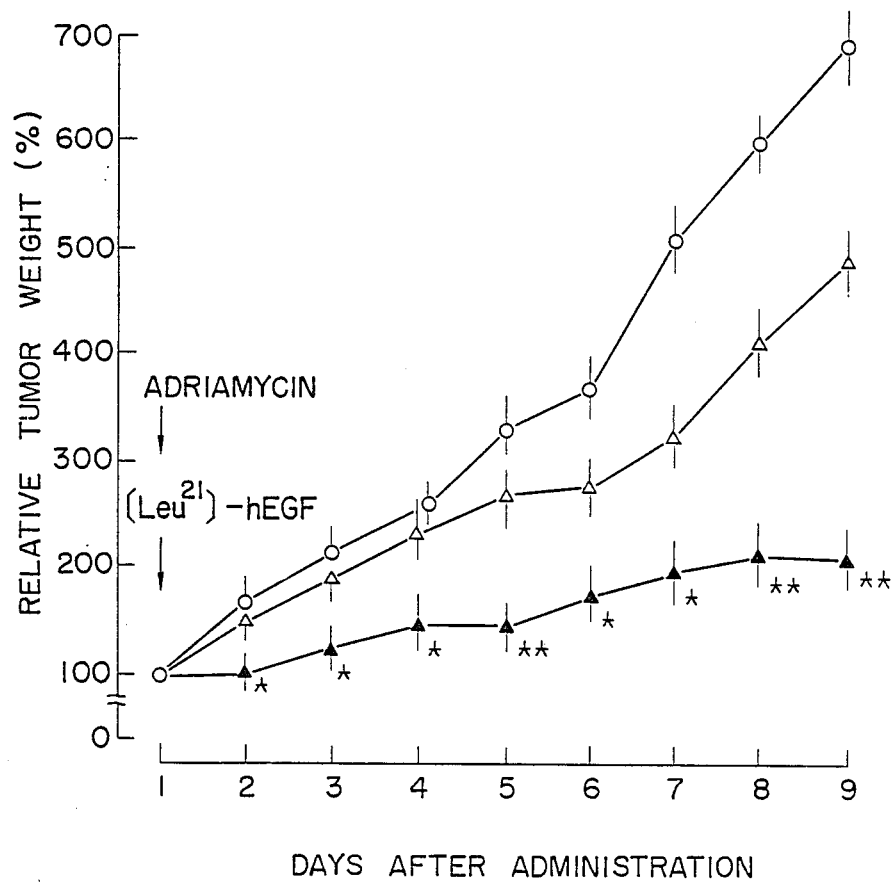
FIG. 7 is a graph showing the change with lapse of time of tumor weight in Experimental Example 10.

The results obtained were as shown in FIG. 7. The symbols in the figure were as follows.

▲: [Leu$^{21}$]-hEGF+adriamycin combined administration group

△: adriamycin administration group Others are the same as above.

From these results, remarkable tumor growth inhibiting effect was recognized on the next day after administration by combined administration of 10 mg/Kg of adriamycin and 100 μg/Kg of [Leu$^{21}$]-hEGF, and the size became only about 1.5-fold of that on the administration day even on the day 9 after administration. In contrast, when 10 mg/Kg of adriamycin was administered singly subcutaneously, the size reached about 5-fold of that on the administration day on the day 9 after administration, thus indicating slight antitumore effect as compared with the no compound administration group, but the effect was not so strong as when [Leu$^{21}$]-hEGF was administered in combination.

In the group to which [Leu$^{21}$]-hEGF and adriamycin were administered in combination, a statistically significant and persistent antitumor action potentiating effect was recognized relative to the tumor weight in the group to which adriamycin was administered singly.

Experimental Example 11

By use of adriamycin which is an antibiotic type antitumor agent, the hEGF antitumor action potentiating effect against human breast cancer was examined.

The antitumor action was assayed by measurement of increase or decrease of tumor weight.

(1) Experimental animals

After BALB/c AJcl-nu strain male nude mice were preliminarily fed for one week in an aseptic clean rack maintained at a constant temperature, (23±0.5° C.) and a constant humidity (60±5%), those which appeared to be healthy weighing around 20 g were provided for the present experiment in 8 mice per group. The mice employed in the present experiments hereinafter were fed under the above environment.

(2) Experimental method and results

MX-1 (human breast cancer) was cut into sizes of about 1 mm square and transplanted subcutaneously on the right side of mouse axilla by a cell transplanting needle (trocker). 17 days after transplantation, the size of tumor, namely the longer diameter (a mm) and shorter diameter (b mm) were measured and the tumor weight was calculated by the following formula similarly as for Colon 26.

$$\text{Tumor weight } (mg) = ab^2/2$$

[Since the tumor phyma takes generally a shape of a spheroid, the formula for calculation of the volume of spheroid was introduced. Also, with the specific gravity of tumor cell as being about 1, volume was made equal to weight].

Before carrying out experiments, tumor weights were measured immediately before administration of the compounds (the day 17 after tumor transplantation) and the mice were grouped into 3 groups by use of random numbers so that there may be no difference in average value of the tumor weights on initiation of experiments between the respective groups to make even the average values of tumor weights of the respective groups, and thereafter the compounds were administered to the respective groups.

In order to see the antitumor action potentiating effect by the growth factor of the present invention, measurement of tumor weight was carried out for a group to which 10 mg/Kg of adriamycin which has been frequently used in the prior art as a compound having antitumor action, a group to which 10 mg/Kg of adriamycin and 100 μg/Kg of hEGF were administered in combination and a group to which no compound was administered. The results obtained were as shown in Table 4.

In the Table, the days indicate the experimental days with the day of compound administration being the day 1, and the tumor weight immediately before compound abstraction on the day 1 is made 100.

Administration of the compounds was conducted 4 times as the total on the day 1, the day 8, the day 10 and the day 13. The test solutions were as shown below.

hEGF: the same as in Experimental Example 1.

Adriamycin: the same as in Experimental Example 2.

The respective values indicate average value ± standard error of case numbers of 8 mice. The mark ** in the Table indicates that the tumor weight of the combined administration group was inhibited statistically significantly relative to the adriamycin single administration group (the definition of P is the same as above).

From these results, in hEGF+adriamycin combined administration group, significant and persistent tumor cell growth inhibition was recognized on the day 4 after administration and thereafter relative to the adriamycin single administration group.

That is, the potentiating action of antitumor effect could be seen not only against the experimental tumor of mouse but also against human cancer by combined use of hEGF and the antitumor agent.

Accordingly, it is readily conceivable that this preparation can be a useful drug even against human cancer.

TABLE 4

| Days | Group without compound treatment | Adriamycin single administration group | Adriamycin/hEGF combined administration group |
|---|---|---|---|
| 1 | 100 | 100 | 100 |
| 4 | 187.9 ± 7.8 | 162.0 ± 5.4 | 130.0 ± 7.7** |
| 7 | 356.0 ± 24.9 | 221.8 ± 20.1 | 160.2 ± 17.7* |
| 11 | 564.2 ± 51.4 | 291.8 ± 21.3 | 201.8 ± 13.9** |
| 14 | 742.6 ± 90.3 | 256.9 ± 12.7 | 99.5 ± 9.3** |

By use of mytomycin c and cisplatin in place of adriamycin, the same experiment as above was conducted for the effects of combined uses of each of them with hEGF, [Leu$^{21}$]-hEGF or hEGF-II. As the result, the same results as above were obtained.

Experimental Example 12

By use of hEGF-II which is a fragment of hEGF lacking two amino acid residues on the C-terminal side of the amino acid sequence, the antitumor action potentiating effect was examined similarly as the above Experimental Example 1.

Although hEGF-II is a fragment of hEGF, its binding ability of receptor or biological activity is equal to hEGF as mentioned above.

Experimental method and results

The experiment was carried out in the same manner as in Experimental Example 1. However, the test solution administration groups were made a group to which 150 mg/Kg of 5-FU was administered singly subcutaneously, a group to which 150 mg/Kg of 5-FU and 100 μg/Kg of hEGF-II were administered in combination subcutaneously and a compound to which no compound was administered.

The results obtained were as shown in Table 5.

In the Table, the days indicate the experimental days with the compound administration day as the day 1, and the tumor weight immediately before administration of the compound on the day 1 is made 100. The respecive values indicate average value ± standard error of 6–12 mice. In the Table, the marks (*), *, and ** indicate statistical significance difference of the combined administration group relative to the 5-FU single administration group (the definition of P is the same as above).

From these results, in any of the hEGF-II +5-FU combined use administration group, significant and persistent tumor cell inhibition could be recognized relative to the tumor weight of the 5-FU single administration grup on the next dy after administration.

TABLE 5

| Days | Group without compound treatment | 5-FU single administration group | hEGF-II/5-FU combined administration group |
|---|---|---|---|
| 1 | 100 | 100 | 100 |
| 2 | 169.9 ± 10.2 | 121.1 ± 9.6 | 100.0 ± 5.9(*) |
| 3 | 215.6 ± 7.6 | 120.4 ± 7.1 | 99.8 ± 7.2(*) |
| 4 | 307.2 ± 31.9 | 124.0 ± 9.6 | 81.3 ± 5.5** |
| 5 | 330.2 ± 35.2 | 122.5 ± 10.7 | 97.5 ± 8.4(*) |
| 6 | 367.3 ± 45.3 | 129.7 ± 11.5 | 93.3 ± 5.8* |
| 7 | 508.9 ± 61.3 | 156.8 ± 14.1 | 93.7 ± 5.9** |

Experimental Example 13

By use of [Leu$^{21}$]-hEGF which is an hEGF derivative in which the 21st methyonine from the N-terminal of the amino acid sequence of hEGF is substituted with leucine (Leu), the antitumore action potentiating effect was examined similarily as in the above Experimental Example 1.

Experimental method and results

The experiment was conducted in the same manner as in Experimental Example 1.

However, the test administration groups were made a group to which 150 mg/Kg of 5-FU was administered singly subcutaneously, a group to which 150 mg/Kg of 5-FU and 100 μg/Kg of [Leu$^{21}$]-hEGF were administered in combination subcutaneously and a group to which no compound was obtained.

Figure 8:
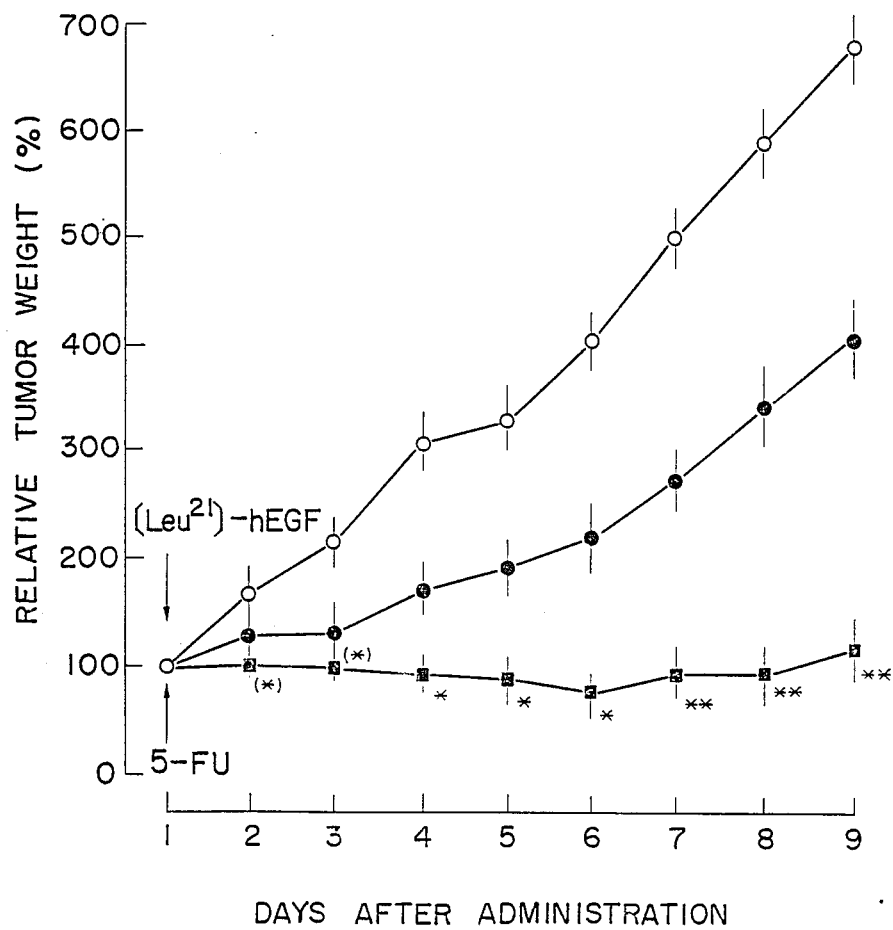
FIG. 8 is a graph showing the change with lapse of time of tumor weight in Experimental Example 13.

The results obtained were as shown in FIG. 8. The symbols in the Figure have the following meanings.

○: no compound administration group.
●: 5-FU administration group.
■: [Leu$^{21}$]-hEGF+5-FU combined administration group The test solutions were as follows.

[Leu21]-hEGF: a solution dissolved in a solvent (physiological saline of pH 7.4 containing 0.01% Tween 80) to 100 μg/10 ml/Kg.

5-FU: the same as in Experimental Example 1.

From these results, by combined use of 100 μg/Kg of [Leu$^{21}$]-hEGF and 150 mg/Kg of 5-FU, remarakable tumor growth inhibiting effect was recognized on the next day after administration, and the size of tumor was suppressed to substantially the same extent as on the administration day t the day 9 after administration. As compared with the 5-FU single administration group, the size remained about ¼ even after the day 9. As attached with the marks (*), *, **, also statistically significant persistent antitumor effect potentiating action was recognized as compared with the 5-FU single administration group.

Also, by use of cyclophosphamide which is an alkylating agent in place of 5-FU, the same experiment as above was conducted for each of the combinations thereof with hEGF or hEGF-II, and the same results were obtained.

Experimental Example 14

By use of Tegafur (Ftrafur) which is changed to 5-fluorouracil (5-FU) by metabolism in a living body, the antitumor potentiating effect was examined in the same manner as in Experimental Example 4.

The experiment was carried out in the same manner as in Experimental Example 4 except that the test solution administration groups were made a group to which 400 mg/Kg Tegafur was administered singly subcutaneously, a group to which 400 mg/Kg of Tegafur and 100

μg/Kg of hEGF were administered in combination subcutaneously and a group without treatment of compound.

Administration of the compounds was conducted twice as the total on the day 1 and the day 4. The test solutions were as follows.

hEGF: the same as in Experimental Example 1.

Tegafur: Ftrafur ® (Taiho Yakuhin Kogyo K.K.) was used at a dose of 400 mg/10 ml/Kg.

The results obtained were as shown in Table 6. In the Table, the days indicate the experimental days with the day of the first administration of compound being as the day 1, and the tumor weight immediately before administration of the compound on the day 1 is made 100. The respective values show average value±standard error of 7 mice. In the Table, the marks *, ** indicate that the tumor weight of the combined administration group was inhibited statistically significantly relative to the Tegafur single administration group (the definition of P is the same as above).

From these results, in the hEGF+Tegafur combined administration group, significant and persistent tumor cell growth inhibition was recognized relative to the Tegafur single administration group on the next day after administration.

Also, when the same experiment was conducted by use of [Leu$^{21}$]-hEGF or hEGF-II in place of hEGF, the same results were obtained.

TABLE 6

| Days | Group without compound treatment | Tegafur single administration group | Tegafur/hEGF combined administration group |
| --- | --- | --- | --- |
| 1 | 100 | 100 | 100 |
| 2 | 182.8 ± 42.1 | 89.0 ± 10.5 | 50.9 ± 11.1* |
| 3 | 208.8 ± 37.5 | 102.1 ± 13.5 | 32.8 ± 10.2** |
| 4 | 240.4 ± 25.5 | 105.5 ± 18.4 | 34.1 ± 12.4** |
| 5 | 301.6 ± 21.3 | 104.2 ± 22.6 | 27.7 ± 5.0* |
| 6 | 380.7 ± 24.2 | 94.5 ± 16.9 | 30.6 ± 8.3* |
| 7 | 448.3 ± 50.2 | 131.4 ± 23.3 | 11.4 ± 5.4** |
| 8 | 560.2 ± 48.1 | 143.7 ± 20.6 | 17.0 ± 4.2** |

Experimental Example 15

By use of cyclophosphamide which is classified into the field of alkylating agent among antitumor agents, the antitumor action potentiating effect was examined similarly as in Experimental Example 4. The experiment was carried out in the same manner as in Experimental Example 4, except that the test solution administration groups were made a group to which 200 mg/Kg of cyclophosphamide was administered singly subcutaneously, a group to which 200 mg/Kg of cyclophosphamide and 100 μg/Kg of hEGF were administered in combination subcutaneously and a group without treatment of compound.

The test solutions were as follows.

hEGF: the same as in Experimental Example 1.

Cyclophosphamide: a solution of cyclophosphamide dissolved in physiological saline to 200 mg/10 ml/Kg.

The results obtained were as shown in Table 7.

The compound was administered first on the day 1 and secondarily on the day 3. In the Table, the days indicate the experimental days with the first compound administration date being the day 1, and the tumor weight immediately before administration of the compound on the day 1 is made 100. The respective values indicate average value±standard error of 8 mice. In the Table, the marks *, ** indicate that the tumor weight of the combined administration group was statistically insignificantly inhibited relative to the cyclophosphamide single administration group (the definition of P is the same as above).

From these results, in the hEGF+cyclophosphamide combined administration group, significant and persistant tumor cell growth inhibiting effect could be recognized relative to the cyclophosphamide single administration group on the next day after administration.

TABLE 7

| Days | Group without compound treatment | Cyclophosphamide single administration group | hEGF/Cyclophosphamide combined administration group |
| --- | --- | --- | --- |
| 1 | 100 | 100 | 100 |
| 2 | 194.9 ± 58.1 | 145.2 ± 18.2 | 99.4 ± 10.0* |
| 3 | 239.8 ± 57.6 | 147.6 ± 13.7 | 95.4 ± 13.5* |
| 4 | 282.5 ± 15.5 | 102.4 ± 8.6 | 69.4 ± 5.2** |
| 5 | 313.6 ± 21.3 | 92.2 ± 5.1 | 69.6 ± 6.7* |
| 6 | 415.6 ± 24.2 | 108.5 ± 19.6 | 54.5 ± 13.2* |
| 7 | 524.5 ± 50.6 | 110.9 ± 21.3 | 43.8 ± 13.6* |

When the same experiment as above was conducted by use of [Leu$^{21}$]-hEGF in place of hEGF, the same results were obtained.

Experimental Example 16

By use of mitomycin C (MMC) which is an antibiotic type antitumor agent, the antitumor potentiating effect was examined in the same manner as in Experimental Example 4. The experiment was conducted in the same manner as in Experimental Example 4 except that the test solution administration groups were made a group to which 5 mg/Kg of MMC was administered singly subcutaneously, a group to which 5 mg/Kg of MMC and 100 μg/Kg of hEGF were administered in combination subcutaneously, a group to which 5 mg/Kg of MMC and 100 μg/Kg of hEGF-II were administered in combination subcutaneously, a group to which 5 mg/Kg of MMC and 100 μg/Kg of [Leu$^{21}$]-hEGF were administered in combination subcutaneously, and a group without compound treatment.

The test solutions were as follows.

hEGF: the same as in Experimental Example 1.

hEGF-II: the same as in Experimental Example 8.

[Leu$^{21}$]-hEGF: the same as in Experimental Example 7.

MMC: a solution of MMC dissolved in distilled water to 5 mg/10 ml/Kg which was made isotonic with body fluid.

The results obtained were as shown in Table 8.

The compounds were administered first on the day 1 and secondarily on the day 5. In the Table, the days indicate the experimental days with the first compound administration date being the day 1, and the tumor weight immediately before compound administration on the day 1 is made 100. The respective values indicate average value±standard error of 6 mice. In the Table, the marks *, ** indicate that the tumor weight of the respective combined administration groups was statistically significantly inhibited relative to the MMC single administration group (the definition of P is the same as above).

From these results, in the combined administration groups of hEGF+MMC, hEGF-II+MMC, and [Leu$^{21}$]-hEGF+MMC, significant and persistent tumor cell growth inhibiting effect could be recognized on the next day after administration.

TABLE 8

| Days | Group without compound treatment | MMC single administration group | hEGF/MMC combined administration group | hEGF-II/MMC combined administration group | [Leu$^{21}$]-hEGF/MMC combined administration group |
|---|---|---|---|---|---|
| 1 | 100 | 100 | 100 | 100 | 100 |
| 2 | 194.9 ± 58.1 | 130.8 ± 8.5 | 97.2 ± 5.1** | 90.5 ± 10.1* | 100.1 ± 5.1* |
| 3 | 239.8 ± 57.6 | 106.1 ± 9.4 | 96.6 ± 5.7 | 98.3 ± 5.6 | 81.3 ± 28.1 |
| 4 | 282.5 ± 15.5 | 95.8 ± 5.5 | 72.2 ± 5.7* | 80.3 ± 9.2 | 85.6 ± 29.1 |
| 5 | 313.6 ± 21.3 | 98.6 ± 3.9 | 68.6 ± 10.5* | 54.4 ± 6.3** | 86.3 ± 14.3 |
| 6 | 415.6 ± 24.2 | 160.7 ± 10.9 | 90.0 ± 10.3** | 64.3 ± 10.8** | 75.4 ± 8.9** |
| 7 | 524.5 ± 50.6 | 150.8 ± 15.9 | 100.1 ± 6.7* | 98.8 ± 6.7* | 88.1 ± 9.6** |
| 8 | 590.6 ± 61.5 | 263.6 ± 30.8 | 130.3 ± 30.3* | 144.4 ± 28.1* | 160.3 ± 15.8* |
| 9 | 603.3 ± 28.9 | 308.7 ± 54.0 | 138.9 ± 21.8* | 156.3 ± 14.3* | 182.4 ± 30.8(*) |

Experimental Example 17

By use of cisplatin which is a platinum preparation, the antitumor action potentiating effect by combined use of each of hEGF, [Leu$^{21}$]-hEGF, hEGF-II with cisplatin against solid tumor of mouse ovarian tumor M5076 was assayed by measuring increase or decrease of tumor weight.

(1) Experimental animals

BDF$_1$ male mice were employed. The feeding conditions were the same as in Experimental Example 1.

(2) Experimental method and experimental results

Mouse ovarian tumor M5076 was transplanted subcutaneously at the axialla of mouse in 1–2×10$^6$ cells per mouse. 12 days after transplantation, the size of tumor was measured according to the same method as in Experimental Example 1 (Colon 26) and the tumor weight was calculated.

The grouping operation on initiation of Experiments was conducted in the same manner as in Experimental Example 1. The compounds were administered in the same manner as in Experimental Example 9.

The results obtained were as shown in Table 9. The symbols in the Table have the same meanings as described above.

From these results, it would be possible to say that the combined use of each of hEGF, [Leu$^{21}$]-hEGF and hEGF-II with cisplatin has clearly further potentiated the antitumor effect of cisplatin alone even against ovarian tumor of mouse. This effect was also found to be statistically significant and persistent.

TABLE 9

| Days | Group without compound treatment | Cisplatin single administration group | Cisplatin/hEGF combined administration group | Cisplatin/[Leu$^{21}$]-hEGF combined administration group | Cisplatin/hEGF-II combined administration group |
|---|---|---|---|---|---|
| 1 | 100 | 100 | 100 | 100 | 100 |
| 2 | 144.9 ± 15.9 | 126.4 ± 9.0 | 99.1 ± 6.7* | 100.1 ± 8.7(*) | 95.3 ± 4.8** |
| 3 | 153.9 ± 14.9 | 125.49 ± 8.3 | 105.2 ± 13.2 | 95.6 ± 8.6* | 98.4 ± 6.5* |
| 4 | 194.6 ± 18.2 | 136.9 ± 5.2 | 103.6 ± 11.7* | 101.1 ± 5.6** | 100.1 ± 4.5** |
| 5 | 207.4 ± 20.9 | 143.6 ± 14.5 | 113.6 ± 9.4(*) | 120.3 ± 10.1 | 115.6 ± 6.3(*) |
| 6 | 225.2 ± 19.1 | 192.0 ± 20.6 | 135.4 ± 14.7* | 140.6 ± 24.5 | 144.4 ± 10.8* |

Also, when the same experiment as above was conducted by use of mytomycin C which is an antibiotic in place of cisplatin, and using each of hEGF, [Leu$^{21}$]-hEGF or hEGF-II together therewith, the same results as above were obtained.

Experimental Example 18

Similarly as in Experimental Example 4, by using each of hEGF, [Leu$^{21}$]-hEGF, hEGF-II and 5-FU, the antitumor action potentiating effect against solid tumor of mouse ovarian tumor M5076 was assayed.

The experiment was carried out in the samme manner as in Experimental Examples 1, 7 and as in Experimental Example 17 for others.

The results were as shown in Table 10. The symbols in the Table are as described above.

TABLE 10

| Days | Group without compound treatment | 5-FU single administration group | 5-FU/hEGF combined administration group | 5-FU/[Leu$^{21}$]-hEGF combined administration group | 5-FU/hEGF-II combined administration group |
|---|---|---|---|---|---|
| 1 | 100 | 100 | 100 | 100 | 100 |
| 2 | 144.9 ± 15.9 | 114.7 ± 7.5 | 100.9 ± 7.9 | 98.6 ± 9.8 | 101.3 ± 8.6 |
| 3 | 153.9 ± 14.9 | 115.2 ± 8.3 | 93.8 ± 4.8* | 100.1 ± 5.6 | 89.5 ± 11.3(*) |
| 4 | 194.6 ± 18.2 | 134.6 ± 8.9 | 93.9 ± 9.2** | 95.9 ± 8.3** | 90.3 ± 10.1** |
| 5 | 207.4 ± 20.9 | 187.3 ± 19.3 | 123.9 ± 14.1* | 116.5 ± 20.3* | 134.4 ± 9.8* |
| 6 | 225.2 ± 19.1 | 230.1 ± 29.4 | 140.1 ± 11.8* | 166.4 ± 21.4(*) | 155.5 ± 15.0* |

From these results, it can be clearly seen that the combined use of each of hEGF, [Leu$^{21}$]-hEGF, hEGF-II with 5-FU has further potentiated the antitumor action of 5-FU alone.

This effect was also found to be statistically significant and persistent.

Also, when the same experiment as above was conducted by use of Tegafur in place of 5-FU which is a metabolism antagonist, using each hEGF, and [Leu$^{21}$]-hEGF or hEGF-II together therewith, the same results as above were obtained. Further, when cyclophosphamide which is an alkylating agent was employed, the same results were obtained.

Experimental Example 19

By use of fibroblast growth factod (FGF) which is classified into the platalet-derived growth factor group among the growth factors, etc., the antitumor action potentiating effect was examined in the same manner as the above Experimental Example 4.

Experimental method and results

The experiment was carried out in the same manner as in Experimental Example 4. However, hEGF was changed to FGF.

The test solutions were as follows.
FGF:
a solution of FGF (Toyobo) dissolved in physiological saline containing 0.001% Tween 80 to 100 $\mu m/10$ ml/Kg.
5-FU:
the same as in Experimental Example 1.

The results obtained were as shown in Table 11.

The descriptions in the Table are the same as in the foregoing Experimental Examples. The respective values indicate average value±standard error of 6–8 mice. Statistical significance differences, etc., are the same as in the foregoing Experimental Examples.

From these results, the tumor weight of the FGF+5-FU combined administration group was recognized to exhibit statistically significant persistent tumor growth inhibiting effect relative to the 5-FU single administration group on the next day after administration.

TABLE 11

| Days | Group without compound treatment | 5-FU single administration group | FGF/5-FU combined administration group |
|---|---|---|---|
| 1 | 100 | 100 | 100 |
| 2 | 126.3 ± 12.6 | 102.6 ± 6.7 | 82.8 ± 7.1(*) |
| 3 | 132.3 ± 9.8 | 99.7 ± 7.2 | 76.2 ± 3.6* |
| 4 | 166.7 ± 22.6 | 94.9 ± 8.7 | 68.8 ± 7.6* |
| 5 | 234.5 ± 12.4 | 158.6 ± 22.8 | 71.5 ± 5.8* |

Also, when the same experiment as above was conducted by use of mytomycin C which is an antibiotic, cyclophosphamide which is an alkylating agent or further a cisplatin which is a platinum preparation in place of 5-FU, the same results as above were obtained.

The compounds having antitumor actions are shown below.
Tegafur
400 mg/Kg, subcutaneous administration
5-FU
150 mg/Kg, subcutaneous administration
Mitomycin-C
5 mg/Kg, subcutaneous administration
Cisplatin
5 mg/Kg, subcutaneous administration The experiment was conducted in the same manner as in Experimental Example 4 except that the administration groups were changed to a group to which the above compound was administered singly by the method and at a dose indicated in the Table, a group to which each compound having antitumor action and 50 $\mu g/Kg$ of hIGF-II were administered in combination subcutaneously, and a group without compound treatment.

The test solutions were as follows.
hIGF-II:
a solution of hIGF-II in a solvent (1/15M sodium phosphate buffer of pH 7.7 containing 0.001% Tween 80 to 50 $\mu g/10$ ml/Kg).
Tegafur:
the same as in Experimental Example 14.
5-FU: the same as in Experimental Example 1.
Mytomycin-C: the same as in Experimental Example 16.
Cisplatin:
the same as in Experimental Example 8.

The results obtained were as shown in Table 12. The values in the Table indicate average value±standartd error of 8–10 mice, with the tumor weight immediately before compound administration being 100. In the Table the marks (*), *, ** indicate statistical significance difference of the IGF-II combined administration group relative to the group to which each compound having antitumor action was singly administered (the definition of P is the same as above). The results are values on the day 4 after compound administration.

From these results, in the group administered with both IGF-II and the above compound having antitumor action, remarkable tumor cell growth inhibition was recognized as compared with all of the groups administered singly with each compound having antitumor action.

TABLE 12

| Administration group | Tumor weight ratio (%) |
|---|---|
| No compound treatment group | 205.1 ± 12.3 |
| Tegafur single administration group | 95.2 ± 15.4 |
| IGF-II + Tegafur combined administration group | 49.8 ± 9.5* |
| 5-FU single administration group | 84.5 ± 7.0 |
| IGF-II + 5-FU combined administration group | 50.6 ± 4.8** |
| Mitomycin-C single administration group | 95.8 ± 5.5 |
| IGF-II + mytomycin-C combined adminstration group | 73.4 ± 5.8* |
| Cisplatin single administration group | 145.6 ± 9.1 |
| IGF-II + cisplatin combined administration group | 98.4 ± 8.2** |

Experimental Example 20

By use of hIGF-II of the insulin-like growth factors, in the same experimental system as in the above Experimental Example 4, the antitumor effect by the combined use of HIGF-II and a compound having antitumor effect as shown below was assayed by measuring increase or decrease of tumor weight.

Experimental Example 21

By use of insulin in the same experimental system as in the above Experimental Example 4, the antitumor effect by combined use of insulin with a compound having antitumor action shown below was assayed according to the same method as in the Experimental Example 20.

The compounds having antitumor actions and test solutions are shown below.

| | |
|---|---|
| Tegafur | 400 mg/Kg, subcutaneous administration, the same as Experimental Example 14. |
| Mitomycin-C | 5 mg/Kg, subcutaneous administration, the same as Experimental Example 16. |
| Adriamycin | 10 mg/Kg, subcutaneous administration, the same as Experimental Example 10. |
| Cisplatin | 5 mg/Kg, subcutaneous administration, the same as Experimental Example 8. |
| Insulin was used as follows. | |
| Insulin | 50 m μg/Kg, subcutaneous administration, the same as in Experimental Example 3. |

The results obtained were as shown in Table 13. The values and symbols in the Table were made similar to those in Experimental Example 23.

From these results, in the combined administration group of insulin and the above compound having antitumor action, remarkable antitumor effect could be obtained as compared with all of the groups administered singly with each compound having antitumor action.

TABLE 13

| Administration group | Tumor weight ratio (%) |
|---|---|
| No compound treatment group | 205.1 ± 12.3 |
| Tegafur single administration group | 95.2 ± 15.4 |
| Insulin + Tegafur combined administration group | 56.3 ± 3.2* |
| Mitomycin-C single administration group | 95.8 ± 5.5 |
| Insulin + mitomycin-C combined administration group | 70.6 ± 4.3** |
| Adriamycin single administration group | 102.4 ± 10.4 |
| Insulin + adriamycin combined administration group | 70.2 ± 6.5* |
| Cisplatin single administration group | 145.6 ± 9.1 |
| Insulin + cisplatin combined administration group | 90.6 ± 5.8** |

The results obtained were as shown in Table 14. The symbols in the Table are the same as described in Table 12.

From these results, in the combined administration group of $TGF_\alpha$+each compound having antitumor action, remarkable antitumor effect could be seen.

TABLE 14

| Administration group | Tumor weight ratio(%) |
|---|---|
| No compound treatment group | 205.1 ± 12.3 |
| 5-FU single administration group | 84.6 ± 7.0 |
| $hTGF_\alpha$ + 5-FU combined administration group | 42.3 ± 5.3** |
| Tegafur single administration group | 95.2 ± 15.4 |
| $hTGF_\alpha$ + Tegafur combined administration group | 38.6 ± 8.9** |
| Mytomycin-C single administration group | 95.8 ± 5.5 |
| $hTGF_\alpha$ + mytomycin-C administration group | 69.8 ± 7.8* |
| Adriamycin single administration group | 102.4 ± 10.4 |
| $hTGF_\alpha$ + adriamycin combined administration group | 63.8 ± 8.9* |
| Cisplatin single administration group | 145.6 ± 9.1 |
| $hTGF_\alpha$ + cisplatin combined administration group | 79.8 ± 10.3** |

Experimental Example 22

By use of human transforming growth factor α ($hTGF_\alpha$) of the transforming growth factors, in the same experimental system as in the above Experimental Example 4, the antitumor effect by combined use of $hTGF_\alpha$ with a compound having antitumor action as shown below was assayed by measuring increase or decrease of tumor weight.

The experiment was carried out in the same manner except the administration groups were changed to a group to which each of the compounds having antitumor action shown below was administered singly, a group to which insulin and each of the compounds having antitumor action shown below were administered in combination, and a group without compound treatment.

The test solutions were as follows.

$hTGF_\alpha$: a solution of $hTGF_\alpha$ dissolved in a solvent (1/15M sodium phosphates buffer of pH 5.9 containing 0.001% Tween 80) to 100 μg/10 ml/Kg. Compounds having antitumor action:
5-FU:
the same as in Experimental Example 1.
Tegafur:
the same as in Experimental Example 14.
Mitomycin-C:
the same as in Experimental Example 16.
Adriamycin:
the same as in Experimental Example 10.
Cisplatin:
the same as in Experimental Example 3.

Experimental Example 23

By use of $hTGF_\beta$ and hEGF in the same experimental system as in the above Experimental Example 4, the antitumor effect by combined use of $hTGF_\beta$ and hEGF with a compound having antitumor action shown below assayed by measuring increase or decrease of tumor weight.

The experiment was carried out in the same manner as in Experimental Example 4 except that the test solution administration groups were changed to a group to which each of the compounds having antitumor action shown below was administered singly subcutaneously, a group to which each compound having antitumor action shown below and 50 mg/Kg of $hTGF_\beta$ and 100 μg/Kg of hEGF were administered in combination, and a group without compound treatment.

The test solutions were as follows.
$hTGF_\beta$:
a solution of $hTGF_\beta$ (BTI Co.) in physiological saline containing 0.001% Tween 80 to 50 mg/10 ml/Kg.
hEGF:
the same as in Experimental Example 1. The compounds having antitumor action are shown below.
5-FU:
the same as in Experimental Example 1.
Tegafur:
the same as in Experimental Example 14.
Mytomycin-C:
the same as in Experimental Example 16.
Adriamycin:
the same as in Experimental Example 10.
Cisplatin:

the same as in Experimental Example 3.
Cyclophosphamide:
the same as in Experimental Example 15.

The results obtained were as shown in Table 15. The symbols in the Table are the same as described in Table 12. these results are those on the day 4 after compound administration.

From these results, remarkable antitumor effect could be obtained in the combined administration group of hTGFβ+hEGF+each compound having antitumor action.

TABLE 15

| Administration group | Tumor weight ratio(%) |
| --- | --- |
| No compound treatment group | 216.3 ± 20.4 |
| 5-FU single administration group | 103.3 ± 15.4 |
| hEGF + hTGFβ + 5-FU combined administration group | 43.1 ± 7.8** |
| Tegafur single administration group | 118.0 ± 9.8 |
| hEGF + hTGFβ + Tegafur combined administration group | 32.0 ± 4.0** |
| Mytomycin-C single administration group | 101.1 ± 8.3 |
| hEGF + hTGFβ + mytomycin-C administration group | 70.0 ± 8.4* |
| Adriamycin single administration group | 102.3 ± 11.3 |
| hEGF + hTGFβ + adriamycin combined administration group | 65.5 ± 5.9** |
| Cisplatin single administration group | 139.8 ± 9.9 |
| hEGF + hTGFβ + cisplatin combined administration group | 80.0 ± 4.1** |
| Cyclophosphamide single administration group | 90.6 ± 7.6 |
| hEGF + hTGFβ + cyclophosphamide combined administration group | 42.7 ± 6.5** |

Experimental Example 24

By use of FGF, in the same experimental system as in the above Experimental Example 4, the antitumor effect by combined use of FGF and Tegafur was assayed by measuring increase or decrease of tumor weight.

The experiment was carried out in substantially the same manner as in Experimental Example 19. However, 5-FU was changed to Tegafur.

The results are shown in Table 16.

From these results, the tumor weight in the FGF+Tegafur combined administration group was recognized to exhibit statistically significant antitumor effect at the time point of the day 4 after administration.

TABLE 16

| Administration group | Tumor weight ratio (%) |
| --- | --- |
| No compound treatment group | 189.6 ± 9.8 |
| Tegafur single administration group | 103.1 ± 13.1 |
| FGF + Tegafur combined administration group | 68.3 ± 7.8* |

Experimental Example 25

By use of hEGF, hEGF-II, [Leu$^{21}$]-hEGF and Retinoic acid (RA), in the same experimental system as in the above Experimental Example 4, the antitumor effect by the combined use of Tegafur with hEGF, hEGF-II, [Leu$^{21}$]-hEGF and RA was assayed by measuring increase or decrease of tumor effect. The Experiment was conducted in the same manner as in Example 4 except that the test solution administration groups were changed to a group to which 400 mg/Kg of Tegafur was administered singly subcutaneously, a group to which 400 mg/Kg of Tegafur and each 100 μg/Kg of hEGF, hEGF-II, [Leu$^{21}$]-hEGF and 30 mg/Kg of RA were administered in combination subcutaneously, and a group without compound treatment.

The test solutions were as follows.
hEGF:
the same as in Experimental Example 1.
hEGF-II:
the same as in Experimental Example 7.
[Leu$^{21}$]-hEGF:
the same as in Experimental Example 13.
Retinoic acid (RA):
a solution of Retinoic acid in olive oil to 30 mg/10 ml/Kg.
Tegafur:
the same as in Experimental Example 14.

The results obtained were as shown in Table 17. The symbol in the Table are the same as described in Table 1. These results are those on the day 4 after compound administration.

From these results, remarkable antitumor effect could be obtained in the combined administration groups of Tegafur with hEGF, hEGF-II, [Leu$^{21}$]-hEGF+Retinol.

TABLE 17

| Administration group | Tumor weight ratio (%) |
| --- | --- |
| No compound treatment group | 183.8 ± 24.1 |
| Tegafur single administration group | 90.6 ± 11.5 |
| hEGF + Tegafur combined administration group | 44.0 ± 12.3* |
| hEGF-II + Tegafur combined administration group | 38.6 ± 8.9** |
| [Leu$^{21}$]-hEGF + Tegafur combined administration group | 40.1 ± 7.4** |
| hEGF + RA + Tegafur combined administration group | 20.3 ± 5.8** |
| hEGF-II + RA + Tegafur combined administration group | 28.6 ± 6.4** |
| [Leu$^{21}$]-hEGF + RA + Tegafur combined administration group | 24.1 ± 10.1** |

Experimental Example 26

By use of UFT ® which is a formulation of tegafur and for uracil, the antitumor effect when used in combination with growth factors, etc., was examined in the same manner as in Experimental Example 4.

The experiment was carried out in the same manner as in the Experimental Example 4 except that the test solution administration groups were changed to a group to which 650 mg/Kg of UFT ® was administered singly orally, a group for which 650 mg/Kg of UFT ® (oral administration) and the following growth factor, etc. (subcutaneous administration) were used in combination, and a group without compound treatment.

The test solutions were as follows.
hEGF:
the same as in Experimental Example 1.
hEGF-II:
the same as in Experimental Example 7.
[Leu$^{21}$]-hEGF:
the same as in Experimental Example 13.
hTGF$_α$:
the same as in Experimental Example 22.
hTGF$_β$:
the same as in Experimental Example 23.
FGF:
the same as in Experimental Example 19.
Insulin:
the same as in Experimental Example 3.

hIGF-II:
the same as in Experimental Example 20.
UFT ®:
UFT ® capsules (Taiho Yakuhin Kogyo K.K.) were disintegrated, suspended in 5% aqueous gum arabic solution and orally administered to 650 mg/Kg as UFT ®. The results obtained were as shown in Table 18. The symbols in the Table are the same as described in Table 12.

From these results, remarkable tumor growth inhibiting effect was recognized by combined administration of a growth factor, etc., and UFT ®. The values in Table 18 indicate the tumor weight ratio on the day 2 after administration of compounds, with the weight immediately before a compound as administration being 100.

TABLE 18

| Administration group | Tumor weight ratio (%) |
|---|---|
| No compound treatment group | 110.3 ± 8.7 |
| UFT single administration group | 80.5 ± 7.5 |
| hEGF + UFT combined administration group | 51.7 ± 7.9* |
| hEGF-II + UFT combined administration group | 55.3 ± 6.8* |
| [Leu$^{21}$]-hEGF + UFT combined administration group | 54.6 ± 8.1* |
| hTGF$_\alpha$ + UFT combined administration group | 40.3 ± 5.1** |
| hEGF + hTGF$_\beta$ + UFT combined administration group | 41.2 ± 6.5** |
| FGF + UFT combined administration group | 59.9 ± 5.1* |
| Insulin + UFT combined administration group | 58.6 ± 8.3(*) |
| hEGF-II + UFT combined administration group | 53.8 ± 6.5* |

"UFT" stands for "UFT ®"

Experimental Example 27

The antitumor effect by combined use of each of hEGF, hEGF-II and [Leu$^{21}$]-hEGF with adriamycin against the solid tumor of mouse leukemia resistant to adriamycin which is an anthracycline type antitumor antibiotic was assayed by measuring increase or decrease of tumor weight. The experiment was conducted in substantially the same manner as in Experimental Example 5, except that the tumor cell was changed to P388/Adr., and the compound having antitumor action was changed to adriamycin.

The test solutions were as follows.
hEGF:
the same as in Experimental Example 1.
hEGF-II:
the same as in Experimental Example 7.
[Leu$^{21}$]-hEGF:
the same as in Experimental Example 13.
Adriamycin:
the same as in Experimental Example 2.

The results obtained were shown in Table 19. The symbols in the Table are the same as described in Table 2.

From these results, antitumor effect was recognized not only against 5-FU resistant tumor but also against adriamycin resistant tumor. Accordingly, it is expected that very effective effect would be exhibited against tumors which became resistant to drugs. The values in Table 19 show the values on the day 2 after compound administration, with the weight immediately before administration being 100.

TABLE 19

| Administration group | Tumor weight ratio (%) |
|---|---|
| No compound treatment group | 181.3 ± 8.9 |
| Adriamycin single administration group | 179.1 ± 5.8 |
| hEGF + adriamycin combined administration group | 118.3 ± 6.5** |
| hEGF-II + adriamycin combined administration group | 120.5 ± 5.9** |
| [Leu$^{21}$]-hEGF + adriamycin combined administration group | 119.4 ± 8.5** |

Reference Example 1

For the purpose of setting the action persistent time of hEGF and administration schedule, the persistence of the tumor action potentiating effect of hEGF was examined by use of 5-FU in the same manner as in Experimental Example 4. The experiment was conducted for a group to which 5-FU was administered singly subcutaneously and a group to which 5-FU and hEGF were administered in combination subcutaneously. Of these, in the group to which 5-FU and hEGF were administered in combination subcutaneously, the following 6 groups were set. That is, they are a group to which hEGF was administered 3 days before administration of 5-FU, a group to which hEGF was administered 2 days before administration of 5-FU, a group to which hEGF was administered one day before administration of 5-FU, a group to which 5-FU and hEGF were simultaneously administered, a group to which hEGF was administered one day after administration of 5-FU and a group to which hEGF was administered 2 days after administration of 5-FU. Otherwise, the experiment was carried out in the same manner as in Experimental Example 4.

The results are shown in Table 20. These results were measured 4 days after administration of 5-FU.

TABLE 20

| Treatment | Tumor weight % (average value ± standard error) |
|---|---|
| 5-FU single administration group | 93.9 ± 6.7 |
| hEGF administered 3 days before 5-FU administration | 81.0 ± 8.8 |
| hEGF administered 2 days before 5-FU administration | 76.9 ± 8.4 |
| hEGF administered 1 day before 5-FU administration | 49.7 ± 9.4** |
| 5-FU/hEGF combined administration group | |
| Simultaneous administration of 5-FU and hEGF | 58.8 ± 6.7** |
| hEGF administered 1 day after 5-FU administration | 99.9 ± 8.5 |
| hEGF administered 2 days after 5-FU administration | 112.6 ± 18.5 |

From these results, not only when 5-FU and hEGF are administered at the same time in combination, but also when hEGF was previously administerd one day before administration of 5-FU, a remarkable tumor growth inhibiting effect was recognized.

This is a matter which could not entirely be expected from in vitro experiments, indicating the length of the acting time of hEGF.

From these results, it may be considered to use a method in which a compound having antitumor action such as 5-FU, etc., is administered while permitting hEGF to be released by way of sustained release in a living body, whereby utilizable scope would be greatly expanded.

In the following, some investigations have been made about the administration methods of the active ingredients (a) and (b) of the present invention. This is described as Reference Example 2 below.

Reference Example 2

Concerning the method for using the active ingredients (a) and (b) of the antitumor agent in the present invention, the following experiments were conducted.

That is, when (a) and (b) were administered in combination, a method was attempted to administer these by mixing them into a solution. The same experimental method as in Experimental Example 4 was employed. The test solutions to be administered were the same except that mixed injection was used only when (a) and (b) were used in combination.

(a) Tegafur:
the same as in Experimental Example 14.
Adriamycin:
the same as in Experimental Example 10.
Cisplatin:
the same as in Experimental Example 8.
(b) hEGF:
the same as in Experimental Example 1.
[Leu$^{21}$]-hEGF:
the same as in Experimental Example 13.
hEGF-II:
the same as in Experimental Example 7.
TGF$_\alpha$:
the same as in Experimental Example 22.
Insulin:
the same as in Experimental Example 3.
FGF:
the same as in Experimental Example 19.

TABLE 21

| | (a) | | | | | |
|---|---|---|---|---|---|---|
| | Tegafur | | Adriamycin | | Cisplatin | |
| | Mixed injection | Separate injection | Mixed injection | Separate injection | Mixed injection | Separate injection |
| (b): | | | | | | |
| hEGF | 42.0 | 45.0 | 103.1 | 98.5 | 88.8 | 80.3 |
| [Leu$^{21}$]-hEGF | 48.1 | 50.3 | 99.6 | 97.8 | 90.4 | 100.1 |
| hEGF-II | 47.8 | 42.8 | 105.6 | 103.3 | 102.3 | 96.6 |
| TGF$_\alpha$ | 34.3 | 40.6 | 98.4 | 92.6 | 80.4 | 80.1 |
| Insulin | 58.9 | 48.1 | 110.2 | 121.1 | 105.6 | 110.3 |
| FGF | 50.3 | 55.4 | 89.8 | 99.1 | 78.4 | 86.5 |

From these results, it can be understood that equal effects can be obtained by either mixed injection or separate injection.

Accordingly, this would be beneficial in preparation.

In the following, Examples of antitumor agents of the present invention are shown, but the present invention is not limited by the following examples.

Following the preparation method of injection preparation described in Japanese Pharmacopoeia, General Rule of Preparation, those which are not isotonic may be made isotonic if desired.

(Example 1) Injection preparation

Human EGF was dissolved in pyrogen-free 1/15M phosphate buffer containing 0.1 w/v% gelatin to give a final concentration of 20 μg/ml. For example, when the pH was 7.4, sodium chloride with the final concentration of 75 mM was added. This solution was filtered through a sterilizing membrane system, for example a 0.22 mμ "Millipore" filter ("Millipore is a trade mark) into ampoules so that each ampoule received 5 ml. The ampoules were sealed under sterile conditions.

(Example 2) Injection preparation

Human EGF was dissolved in pyrogen-free 1/15M phosphate buffer containing 0.001 w/v% polyoxyethylene sorbitane fatty acid ester (Polysorbate 80) to give a final concentration of 20 μg/ml. For example, in the case of pH 7.4, sodium chloride with a final concentration of 75 mM was added. This solution was subjected to filtration for removal of microorganisms in the same manner as in Example 1 and dispensed in each in 5 ml into ampoules, followed by sealing.

(Example 3) Freeze-dried injection preparation

In the injection preparation prepared previously in Example 1, mannitol was dissolved to give a final concentration of 2 w/v%. This solution was subjected to filtration for removal of microorganisms in the same manner as in Example 1, then dispensed in each 5 ml into vials made of glass, freezed at −40° C. for 1 hour and lyophilized by means of a freeze dryer at −10° C. and under a vacuum of 0.04 mmHg, followed by sealing under sterile conditions according to a conventional method.

(Example 4) Freeze-dried injection preparation

In the same manner as in Example 3, a freeze-dried injection preparation was prepared from the injection preparation previously prepared in Example 2.

(Example 5) Injection preparation

| | |
|---|---|
| Human EGF | 100 μg |
| Gelatin | 5 mg |
| 5-Fluorouracil | 100 mg |
| Trishydroxymethylaminomethane | 400 mg |
| Distilled water for injection | q.s. |
| (adjusted to pH 8.0 with hydrochloric acid) | |
| per ampoule | 5 ml |

The above formulation was subjected to filtration for removal of microorganisms in the same manner as in Example 1 to prepare an injection preparation.

(Example 6) Injection preparation

| | |
|---|---|
| Human EGF | 100 μg |
| Polyoxyethylene sorbitane fatty acid ester (Polysorbate 80) | 50 μg |
| 5-Fluorouracil | 100 mg |
| Trishydroxymethylaminomethane | 400 mg |
| Distilled water for injection | q.s. |
| (adjusted to pH 8.0 with hydrochloric acid) | |

The above formulation was subjected to filtration for removal of microorganisms in the same manner as in Example 1 to prepare an injection preparation.

(Example 7) Freeze-dried injection preparation

The injection preparation prepared in Example 5 was apportioned into vials made of glass each in 5 ml, freezed at −40° C. for 1 hour and freeze dried by means of a freeze dryer at −10° C. under a vacuum of 0.04 mmHg, followed by sealing under sterile conditions according to a conventional method.

(Example 8) Freeze-dried injection preparation

From the injection preparation prepared in Example 6, a freeze-dried injection preparation was prepared in the same manner as in Example 7.

(Example 9) Freeze-dried injection preparation

Human EGF was dissolved in pyrogen-free isotonic saline containing 0.1 w/v% gelatin to give a final concentration of 20 μg/ml. In this solution, adriamycin hydrochloride was dissolved to the final concentration of 2 mg/ml. From the solution obtained by subjecting this solution to filtration for removal of microorganisms in the same manner as in Example 1, a freeze-dried injection preparation was prepared according to the same procedure as in Example 7.

(Example 10) Freeze-dried injection preparation

Human EGF was dissolved in pyrogen-free isotonic saline containing 0.001 w/v% polyoxyethylene sorbitane fatty acid ester (Polysorbate 80) to give a final concentration of 20 μg/ml. In this solution, adriamycin hydrochloride was dissolved to give a final concentration of 2 mg/ml. From the solution obtained by subjecting this solution to filtration for removal of microorganisms in the same manner as in Example 1, a freeze-dried injection preparation was prepared according to the same procedure as in Example 7.

(Example 11) Freeze-dried injection preparation

Human EGF was dissolved in pyrogen-free isotonic saline containing 0.1 w/v% galatin to give a final concentration of 20 μg/ml. In this solution, mytomycin C was dissolved to give a final concentration of 400 μg/ml with pH being adjusted with sodium hydroxide to pH 8.0. From this solution, according to the same procedure as in Example 7, freeze-dried injection preparation was prepared.

(Example 12) Freeze-dried injection preparation

Human EGF was dissolved in pyrogen-free isotonic saline containing 0.01 w/v% polyoxyethylene sorbitane fatty acid ester (Polysorbate 80) to give a final concentration of 20 μg/ml. In this solution, mitomycin C was dissolved to give a final concentration of 400 μg/ml with pH being adjusted with sodium hydroxide to pH 8.0. From this solution, according to the same procedure as in Example 7, a freeze-dried injection preparation was prepared.

(Example 13) Injection preparation

| | |
|---|---|
| Human EGF | 100 μg |
| Gelatin | 10 mg |
| 1-(2-tetrahydrofulyl)-5-fluorouracil | 400 mg |
| Trishydroxymethylaminomethane | 400 mg |
| Distilled water for injection | q.s. |
| (adjusted to pH 9.5 with hydrochloric acid) | |
| per ampoule | 10 ml |

The above formulation was subjected to filtration for removal of microorganisms, followed by preparation of an injection preparation in the same manner as in Example 1.

(Example 14) Injection preparation

| | |
|---|---|
| Human EGF | 100 μg |
| Polyoxyethylene sorbitane fatty acid ester (Polysorbate 80) | 100 μg |
| 1-(2-tetrahydrofulyl)-5-fluorouracil | 400 mg |
| Trishydroxymethylaminomethane | 400 mg |
| Distilled water for injection | q.s. |
| (adjusted to pH 9.5 with hydrochloric acid) | |
| per ampoule | 10 ml |

The above formulation was subjected to filtration for removal of microorganisms, followed by preparation of an injection preparation in the same manner as in Example 1.

(Example 15) Freeze-dried injection preparation

From the injection preparation prepared previously in Example 13, a freeze-dried injection preparation was prepared in the same manner as in Example 7.

(Example 16) Freeze-dried injection preparation

From the injection preparation prepared previously in Example 14, a freeze-dried injection preparation was prepared in the same manner as in Example 7.

(Example 17) Injection preparation

| | |
|---|---|
| Human EGF | 100 μg |
| Gelatin | 5 mg |
| Cyclophosphamide (anhydride) | 100 mg |
| Sodium chloride | 45 mg |
| Distilled water for injection | q.s. |
| per ampoule | 5 ml |

The above formulation was subjected to filtration for removal of microorganisms, followed by preparation of an injection preparation in the same manner as in Example 1.

(Example 18) Injection preparation

| | |
|---|---|
| Human EGF | 100 μg |
| Polyoxyethylene sorbitane fatty acid ester (Polysorbate 80) | 50 μg |
| Cyclophosphamide (anhydride) | 100 mg |
| Sodium chloride | 45 mg |
| Distilled water for injection | q.s. |
| per ampoule | 5 ml |

The above formulation was subjected to filtration for removal of microorganisms, followed by preparation of an injection preparation in the same manner as in Example 1.

(Example 19) Freeze-dried injection preparation

From the injection preparation prepared previously in Example 17, a freeze-dried injection preparation was prepared in the same manner as in Example 7.

(Example 20) Freeze-dried injection preparation

From the injection preparation prepared previously in Example 18, a freeze-dried injection preparation was prepared in the same manner as in Example 7.

(Example 21) Injection preparation

| | |
|---|---|
| Human EGF | 100 μg |
| Polyoxyethylene sorbitane fatty acid ester (Polysorbate 80) | 500 μg |
| Cisplatin | 25 mg |
| Sodium chloride | 365 mg |
| Mannitol | 500 mg |
| Distilled water for injection | q.s. |
| per vial | 50 ml |
| (adjusted to pH 2.5, and human EGF was dissolved) | |

The solution of the above formulation was subjected to filtration for removal of microorganisms in the same manner as in Example 1, and apportioned into vials made of amber glass, subsequently, the vials were capped and sealed under sterile conditions.

(Example 22) Freeze-dried injection preparation

The solution after filtration for removal of microorganisms of the formulation in Example 21 was apportioned in each 10 ml into vials made of amber glass, followed by preparation of freeze-dried injection preparation.

(Example 23) Injection preparation

Bovine brain FGF was dissolved in pyrogen-free 1/15M phosphate buffer containing 0.1 w/v% gelatin to give a final concentration of 20 μg/ml. For example, in the case of pH 7.4, sodium chloride with the final concentration of 75 mM was added. The solution was subjected to filtration for removal of microorganisms in the same manner as in Example 1, dispensed each in 5 ml into ampoules, followed by sealing.

(Example 24) Injection preparation

Bovine brain FGF was dissolved in pyrogen-free 1/15M phosphate buffer containing 0.001 w/v% polyoxyethylenesorbitane fatty acid ester (Polysorbate 80) to give a final concentration of 20 μg/ml. For example, in the case of pH 7.4, sodium chloride with the final concentration of 75 mM was added. The solution was subjected to filtration for removal of microorganism in the same manner as in Example 1, dispensed each in 5 ml into ampoules, followed by sealing.

(Example 25) Freeze-dried injection preparation

From the injection preparation previously prepared in Example 23, a freeze-dried injection preparation was prepared in the same manner as in Example 3.

(Example 26) Freeze-dried injection preparation

From the injection preparation previously prepared in Example 24, a freeze-dried injection preparation was prepared in the same manner as in Example 3.

(Example 27) Injection preparation

| | |
|---|---|
| Bovine brain acidic FGF | 100 μg |
| Gelatin | 5 mg |
| 5-Fluorouracil | 100 mg |
| Trishydroxymethylaminomethane | 400 mg |
| Distilled water for injection | q.s. |
| (adjusted to pH 8.0 with hydrochloric acid) | |
| per ampoule | 5 ml |

The above formulation was subjected to filtration in the same manner as in Example 1 to prepare an injection preparation.

(Example 28) Injection preparation

| | |
|---|---|
| Bovine brain acidic FGF | 100 μg |
| Polyoxyethylene sorbitane fatty acid ester (Polysorbate 80) | 50 μg |
| 5-Fluorouracil | 100 mg |
| Trishydroxymethylaminomethane | 400 mg |
| Distilled water for injection | q.s. |
| (adjusted to pH 8.0 with hydrochloric acid) | |
| per ampoule | 5 ml |

The above formulation was subjected to filtration in the same manner as in Example 1 to prepare an injection preparation.

(Example 29) Freeze-dried injection preparation

From the injection preparation previously prepared in Example 27, a freeze-dried injection preparation was prepared in the same manner as in Example 7.

(Example 30) Freeze-dried injection preparation

From the injection preparation previously prepared in Example 28, a freeze-dried injection preparation was prepared in the same manner as in Example 7.

(Example 31) Injection preparation

| | |
|---|---|
| Human insulin containing 0.5 ww % zinc (after dissolved in hydrochloric acid, mixed with other components) | 40 I.U. |
| Sodium acetate 3H$_2$O | 1.4 mg |
| Methyl p-oxybenzoate | 1 mg |
| Anhydrous glycerol | 16 mg |
| Polyoxyethylene sorbitane fatty acid ester (Polysorbate 80) | 10 μg |
| Distilled water for injection | q.s. |
| Sodium hydroxide | q.s. |
| (adjusted to pH 7.4) | |
| per vial | 1 ml |

(Example 32) Freeze-dried injection preparation

Human insulin containing 0.5 w/w% zinc was dissolved in a minimum amount of 1N hydrochloric acid. The insulin solution was dissolved in pyrogen-free isotonic saline containing 0.001 w/v% polyoxyethylene sorbitane fatty acid ester (Polysorbate 80) to give a final concentration of 8 I.U./ml. In this solution, adriamycin hydrochloride was dissolved to the final concentration of 2 mg/ml. This solution was subjected to filtration for removal of microorganisms in the same manner as in Example 1.

According to the same procedure as in Example 7, a freeze-dried injection was prepared from this solution.

(Example 33) Injection preparation

| | |
|---|---|
| Human insulin containing 0.5 ww % zinc (after dissolved in hydrochloric acid, mixed with other components) | 40 I.U. |
| Polyoxyethylene sorbitane fatty acid ester (Polysorbate 80) | 250 μg |
| Cisplatin | 25 mg |
| Sodium chloride | 225 mg |
| Mannitol | 250 mg |
| Distilled water for injection | q.s. |
| per vial | 25 ml |

The solution of the above formulation was subjected to filtration for removal of microorganisms, and dispensed in each 25 ml into 50 ml vials made of amber glass. Then, the vials were capped and sealed under sterile conditions.

(Example 34) Injection preparation

| | |
|---|---|
| Human EGF | 100 μg |
| Sodium acetate | 6 mg |
| Methyl p-oxybenzoate | 5 mg |
| Anhydrous glycerol | 80 mg |
| Polyoxyethylene sorbitane fatty acid ester (Polysorbate 80) | 50 μg |
| Distilled water for injection | q.s. |
| Sodium hydroxide (adjusted to pH 7.4) | q.s |
| per vial | 5 ml |

The above formulation was subjected to filtration for removal of microorganisms to prepare an injection in the same manner as in Example 1.

(Example 35) Injection preparation

| | |
|---|---|
| Human EGF | 100 g |
| Phenol | 10 mg |
| Anhydrous glycerol | 80 mg |
| Polyoxyethylene sorbitane fatty acid ester (Polysorbate 80) | 50 μg |
| Distilled water for injection | q.s. |
| Sodium hydroxide (adusted to pH 7.4) | q.s. |
| per vial | 5 ml |

The above formulation was subjected to filtration for removal of microorganism to prepare an injection in the same manner as in Example 1.

(Example 36) Injection preparation

| | |
|---|---|
| Human EGF | 100 μg |
| m-Cresol | 15 mg |
| Anhydrous glycerol | 80 mg |
| Polyoxyethylene sorbitane fatty acid ester (Polysorbate 80) | 50 g |
| Distilled water for injection | q.s. |
| Sodium hydroxide (adjusted to pH 7.4) | q.s. |
| per vial | 5 ml |

The above formulation was subjected to filtration for removal of microorganisms to prepare an injection in the same manner as in Example 1.

(Example 37) Freeze-dried injection preparation

| | |
|---|---|
| Human EGF | 50 μg |

-continued

| | |
|---|---|
| Human EGF-II | 50 μg |
| Polyoxyethylene sorbitane fatty acid ester (Polysorbate 80) | 50 μg |
| 5-Fluorouracil | 100 mg |
| Trishydroxymethylaminomethane | 400 mg |
| Distilled water for injection | q.s. |
| (adjusted to pH 8.0 with hydrochloric acid) | 5 ml |

The above formulation was subjected to filtration for removal of microorganisms in the same manner as in Example 1, and from the resultant solution, a freeze-dried injection preparation was prepared in the same manner as in Example 3.

(Example 38) Freeze-dried injection preparation

| | |
|---|---|
| Human EGF | 50 μg |
| Human EGF-II | 50 μg |
| Polyoxyethylene sorbitane fatty acid ester (Polysorbate 80) | 100 μg |
| 1-(2-Tetrahydrofulyl)-5-fluorouracil | 400 mg |
| Trishydroxymethylaminomethane | 400 mg |
| Distilled water for injection | q.s. |
| (adjusted to pH 9.5 with hydrochloric acid) | 10 ml |

The above formulation was subjected to filtration for removal of microorganisms in the same manner as in Example 1, and from the resultant solution a freeze-dried injection preparation was prepared in the same manner as in Example 3.

(Example 39) Freeze-dried Injection preparation

Human EGF and human EGF-II were dissolved in pyrogen-free isotonic saline containing 0.001 w/v% polyoxyethylene sorbitane fatty acid ester (Polysorbate 80) to give a final concentrations of 10 μg/ml (human EGF) and 10 μg/ml (human EGF-II). In this solution, adriamycin hydrochloride was dissolved to give a final concentration of 2 mg/ml. This solution was subjected to filtration for removal of microorganisms in the same manner as in Example 1, and from the resultant solution a freeze-dried injection preparation was prepared according to the same procedure as in Example 7.

(Example 40) Freeze-dried injection preparation

Human EGF and human EGF-II were dissolved in a pyrogen-free physiological saline containing 0.001 w/v% polyoxyethylene sorbitane fatty acid ester (Polysorbate 80) to the final concentrations of 10 μg/ml (human EGF) and 10 μg/ml (human EGF-II). In this solution, mytomycin C was dissolved to the final concentration of 400 μg/ml, with pH being adjusted to 8.0 with sodium hydroxide. From this solution, according to the same procedure as in Example 7, a freeze-dried injection preparation was prepared.

(Example 41) Injection preparation

| | |
|---|---|
| Human EGF | 50 μg |
| Human EGF-II | 50 μg |
| Polyoxyethylene sorbitane fatty acid ester (Polysorbate 80) | 500 μg |
| Cisplatin | 25 mg |
| Sodium hydrochloride | 365 mg |
| Mannitol | 500 mg |
| Distilled water for injection | q.s. |
| per vial | 50 ml |
| (adjusted to pH 2.5 with hydrochloric acid) | |

The solution of the above formulation was subjected to filtration for removal of microorganisms in the same manner as in Example 1 and apportioned each in 50 ml into vials made of amber glass. Then, the vials were capped and sealed under sterile conditions.

(Example 42) Freeze-dried injection preparation

| [Leu$^{21}$]-human EGF | 100 μg |
|---|---|
| Polyoxyethylene sorbitane fatty acid ester (Polysorbate 80) | 50 μg |
| 5-Fluorouracil | 100 mg |
| Trishydroxymethylaminomethane | 400 mg |
| Distilled water for injection | q.s. |
| (adjusted to pH 8.0 with hydrochloric acid) | 5 ml |

The above formulation was subjected to filtration for removal of microorganisms in the same manner as in Example 1, and from the resultant solution, a freeze-dried injection preparation was prepared in the same manner as in Example 3.

(Example 43) Freeze-dried injection preparation

| [Leu$^{21}$]-human EGF | 100 μg |
|---|---|
| Polyoxyethylene sorbitane fatty acid ester (Polysorbate 80) | 100 μg |
| 1-(2-Tetrahydrofulyl)-5-fluorouracil | 400 mg |
| Trishydroxymethylaminomethane | 400 mg |
| Distilled water for injection | q.s. |
| (adjusted to pH 9.5 with hydrochloric acid) | 10 ml |

The above formulation was subjected to filtration for removal of microorganisms in the same manner as in Example 1, and from the resultant solution, a freeze-dried injection preparation was prepared in the same manner as in Example 3.

(Example 44) Freeze-dried injection preparation

[Leu$^{21}$]-human EGF were dissolved inn pyrogen-free isotonic saline containing 0.001 w/v% polyoxyethylene sorbitane fatty acid ester (Polysorbate 80) to the final concentration of 20 μg/ml. In this solution, adriamycin hydrochloride was dissolved to give a final concentration of 2 mg/ml. This solution was subjected to filtration for removal of microorganisms in the same manner as in Example 1, and from the resultant solution a freeze-dried injection preparation was prepared according to the same procedure as in Example 7.

(Example 45) Freeze-dried injection preparation

[Leu$^{21}$]-human EGF were dissolved in pyrogen-free isotonic saline containing 0.001 w/v% polyoxyethylene sorbitane fatty acid ester (Polysorbate 80) to give a final concentration of 20 μg/ml. In this solution, mytomycin C was dissolved to the final concentration of 400 μg/ml, with pH being adjusted to 8.0 with sodium hydroxide. From this solution, according to the same procedure as in Example 7, a freeze-dried injection preparation was prepared.

(Example 46) Injection preparation

| [Leu$^{21}$]-human EGF | 100 μg |
|---|---|
| Polyoxyethylene sorbitane fatty acid ester (Polysorbate 80) | 500 μg |
| Cisplatin | 25 mg |
| Sodium hydrochloride | 365 mg |
| Mannitol | 500 mg |
| Distilled water for injection | q.s. |
| per vial | 50 ml |
| (adjusted to pH 2.5 with hydrochloric acid) | |

The solution of the above formulation was subjected to filtration for removal of microorganisms in the same manner as in Example 1 and apportioned each in 50 ml into vials made of amber glass. Then, the vials were capped and sealed under sterile conditions.

(Example 47) Freeze-dried injection preparation

| Human TGF$_\alpha$ | 100 μg |
|---|---|
| Polyoxyethylene sorbitane fatty acid ester (Polysorbate 80) | 50 μg |
| 5-Fluorouracil | 100 mg |
| Trishydroxymethylaminomethane | 400 mg |
| Distilled water for injection | q.s. |
| (adjusted to pH 8.0 with hydrochloric acid) | 5 ml |

The above formulation was subjected to filtration for removal of microorganisms in the same manner as in Example 1, and from the resultant solution, a freeze-dried injection preparation was prepared in the same manner as in Example 3.

(Example 48) Freeze-dried injection preparation

| Human TGF$_\alpha$ | 100 μg |
|---|---|
| Polyoxyethylene sorbitane fatty acid ester (Polysorbate 80) | 100 μg |
| 1-(2-Tetrahydrofulyl)-5-fluorouracil | 400 mg |
| Trishydroxymethylaminomethane | 400 mg |
| Distilled water for injection | q.s. |
| (adjusted to pH 9.5 with hydrochloric acid) | 10 ml |

The above formulation was subjected to filtration for removal of microorganisms in the same manner as in Example 1, and from the resultant solution, a freeze-dried injection preparation was prepared in the same manner as in Example 3.

(Example 49) Injection preparation

| Human TGF$_\alpha$ | 100 μg |
|---|---|
| Polyoxyethylene sorbitane fatty acid ester (Polysorbate 80) | 500 μg |
| Cisplatin | 25 mg |
| Sodium hydrochloride | 365 mg |
| Mannitol | 500 mg |
| Distilled water for injection | q.s. |
| per vial | 50 ml |
| (adjusted to pH 2.5 with hydrochloric acid) | |

The solution of the above formulation was subjected to filtration for removal of microorganisms in the same manner as in Example 1 and dispensed each in 50 ml into vials made of amber glass. Then, the vials were capped and sealed under sterile conditions.

(Example 50) Freeze-dried injection preparation

| Human EGF | 100 μg |
|---|---|
| Human TGF$_\beta$ | 50 mg |
| Polyoxyethylene sorbitane fatty acid ester (Polysorbate 80) | 50 μg |
| 5-Fluorouracil | 100 mg |
| Trishydroxymethylaminomethane | 400 mg |
| Distilled water for injection | q.s. |

The above formulation was subjected to filtration for removal of microorganisms in the same manner as in Example 1, and from the resultant solution, a freeze-dried injection preparation was prepared in the same manner as in Example 3.

(Example 51) Freeze-dried injection preparation

| Human EGF | 100 μg |
|---|---|
| Human TGFβ | 50 mg |
| Polyoxyethylene sorbitane fatty acid ester (Polysorbate 80) | 100 μg |
| 1-(2-Tetrahydrofulyl)-5-fluorouracil | 400 mg |
| Trishydroxymethylaminomethane | 400 mg |
| Distilled water for injection | q.s. |
| (adjusted to pH 9.5 with hydrochloric acid) | 10 ml |

The above formulation was subjected to filtration for removal of microorganisms in the same manner as in Example 1, and from the resultant solution, a freeze-dried injection preparation was prepared in the same manner as in Example 3.

(Example 52) Freeze-dried injection preparation

| Bovine brain acidic FGF | 100 μg |
|---|---|
| Polyoxyethylene sorbitan fatty acid ester (Polysorbate 80) | 100 μg |
| 1-(2-Tetrahydrofulyl)-5-fluorouracil | 400 mg |
| Trishydroxymethylaminomethane | 400 mg |
| Distilled water for injection | q.s. |
| (adjusted to pH 9.5 with hydrochloric acid) | 10 ml |

The above formulation was subjected to filtration for removal of microorganisms in the same manner as in Example 1, and from the resultant solution, a freeze-dried injection preparation was prepared in the same manner as in Example 3.

(Example 53) Freeze-dried injection preparation

Human insulin containing 0.5 w/w% zinc was dissolved in a minimum amount of 1N hydrochloric acid. The insulin solution was dissolved in pyrogen-free isotonic saline containing 0.001 w/v% polyoxyethylene sorbitane fatty acid ester (Polysorbate 80) to give a final concentration of 8 I.U./ml. In this solution, mitomycin C was dissolved to give a final concentration of 400 μg/ml with pH being adjusted to 8 with sodium hydroxide. The solution was subjected to filtration for removal of microorganisms in the same manner as in Example 1, and from the resultant solution according to the same procedure as in Example 7, freeze-dried injection preparation was prepared.

(Example 54) Freeze-dried injection preparation

| Human IGF-II | 50 μg |
|---|---|
| Polyoxyethylenesorbitane fatty acid ester (Polysorbate 80) | 50 μg |
| 5-Fluorouracil | 100 mg |
| Trishydroxymethylaminomethane | 400 mg |
| Distilled water for injection | q.s. |
| (adjusted to pH 8.0 with hydrochloric acid) | 5 ml |

The above formulation was subjected to filtration for removal of microorganisms in the same manner as in Example 1, and from the resultant solution, a freeze-dried injection preparation was prepared in the same manner as in Example 3.

(Example 55) Freeze-dried injection preparation

| Human IGF-II | 50 μg |
|---|---|
| Polyoxyethylene sorbitane fatty acid ester (Polysorbate 80) | 100 μg |
| 1-(2-Tetrahydrofulyl)-5-fluorouracil | 400 mg |
| Trishydroxymethylaminomethane | 400 mg |
| Distilled water for injection | q.s |
| (adjusted to pH 9.5 with hydrochloric acid) | 10 ml |

The above formulation was subjected to filtration for removal of microorganisms in the same manner as in Example 1, and from the resultant solution, a freeze-dried injection preparation was prepared in the same manner as in Example 3.

(Example 56) Freeze-dried injection preparation

Human IGF-II was dissolved in pyrogen-free isotonic saline containing 0.001 w/v% polyoxyethylene sorbitane fatty acid ester (Polysorbate 80) and 0.001N hydrochloric acid to give a final concentration of 10 μg/ml. In this solution, adriamycin hydrochloride was dissolved to give a final concentration of 2 mg/ml. This solution was subjected to filtration for removal of microorganisms in the same manner as in Example 1, and from the resultant solution a freeze-dried injection preparation was prepared according to the same procedure as in Example 7.

(Example 57) Freeze-dried injection preparation

Human IGF-II was dissolved in pyrogen-free isotonic saline containing 0.001 w/v% polyoxyethylene sorbitane fatty acid ester (Polysorbate 80) adjusted to pH 8.0 with sodium hydroxide to give a final concentration of 10 μg/ml. In this solution, mytomycin C was dissolved to the final concentration of 400 μg/ml. The solution was subjected to filtration for removal of microorganisms in the same manner as in Example 1, and from the resultant solution a freeze-dried injection preparation was prepared according to the same procedure as in Example 7.

(Example 58) Injection preparation

| Human IGF-II | 50 μg |
|---|---|
| Polyoxyethylene sorbitane fatty acid ester (Polysorbate 80) | 500 μg |
| Cisplatin | 25 mg |
| Sodium hydrochloride | 365 mg |
| Mannitol | 500 mg |
| Distilled water for injection | q.s. |
| per vial | 50 ml |
| (adjusted to pH 2.5 with hydrochloric acid, and human IGF-II was dissolved) | |

The solution of the above formulation was subjected to filtration for removal of microorganisms in the same manner as in Example 1 and dispensed each in 50 ml into vials made of amber glass. Then, the vials were capped and sealed under sterile conditions.

(Example 59) Freeze-dried injection preparation

Human EGF and human EGF-II were dissolved in pyrogen-free 1/15M sodium phosphate buffer containing 0.1 w/v% of gelatin to give a final concentration of 10 μg/ml. With the pH being adjusted to 7.4, sodium chloride with the final concentration of 75 mM was added. This solution was subjected to filtration for removal of microorganisms in the same manner as in Example 1, and from the resultant solution, a freeze-dried injection preparation was prepared in the same manner as in Example 3.

(Example 60) Freeze-dried injection preparation

Human EGF and human EGF-II were dissolved in pyrogen-free 1/15M sodium phosphate buffer containing 0.001 w/v% of polyoxyethylene sorbitane fatty acid ester (Polysorbate 80) to give a final concentration of 10 μg/ml. With the pH being adjusted to 7.4, sodium chloride with the final concentration of 75 mM was added. This solution was subjected to filtration for removal of microorganisms in the same manner as in Example 1, and from the resultant solution, a freeze-dried injection preparation was prepared in the same manner as in Example 3.

(Example 61) Freeze-dried injection preparation

[Leu$^{21}$]-hEGF was dissolved in pyrogen-free 1/15M sodium phosphate buffer containing 0.1 w/v% of gelatin to give a final concentration of 20 μg/ml. With the pH being adjusted to 7.4, sodium chloride with the final concentration of 75 mM was added. This solution was subjected to filtration for removal of microorganisms in the same manner as in Example 1, and from the resultant solution, freeze-dried injection preparation was prepared in the same manner as in Example 3.

(Example 62) Freeze-dried injection preparation

[Leu$^{21}$]-hEGF was dissolved in pyrogen-free 1/15M sodium phosphate buffer containing 0.001 w/v% of polyoxyethylene sorbitane fatty acid ester (Polysorbate 80) to give a final concentration of 20 μg/ml. With the pH being adjusted to 7.4, sodium chloride with the final concentration of 75 mM was added. This solution was subjected to filtration for removal of microorganisms in the same manner as in Example 1, and from the resultant solution, freeze-dried injection preparation was prepared in the same manner as in Example 3.

(Example 63) Injection preparation

Human TGF$_\alpha$ was dissolved in pyrogen-free 1/15M sodium phosphate buffer containing 0.1 w/v% of gelatin to give a final concentration of 20 μg/ml. With the pH being adjusted to 7.4, sodium chloride with the final concentration of 75 mM was added. This solution was subjected to filtration for removal of microorganisms in the same manner as in Example 1, and from the resultant solution, and apportioned in each 5 ml into ampoules, followed by sealing.

(Example 64) Injection preparation

Human TGF$_\alpha$ was dissolved in pyrogen-free 1/15M sodium phosphate buffer containing 0.001 w/v% of polyoxyethylene sorbitane fatty acid ester (Polysorbate 80) to give a final concentration of 20 μg/ml. With the pH being adjusted to 7.4, sodium chloride with the final concentration of 75 mM was added. This solution was subjected to filtration for removal of microorganisms in the same manner as in Example 1, and from the resultant solution, and dispensed in each 5 ml into ampoules, followed by sealing.

(Example 65) Freeze-dried injection preparation

Human EGF and human TGF$_\beta$ were dissolved in pyrogen-free 1/15M sodium phosphate buffer containing 0.1 w/v% of gelatin to give a final concentrations of 20 μg/ml and 10 mg/ml, respectively. With the pH being adjusted to 7.4, sodium chloride with the final concentration of 75 mM was added. This solution was subjected to filtration for removal of microorganisms in the same manner as in Example 1, and from the resultant solution, freeze-dried injection preparation was prepared in the same manner as in Example 3.

(Example 66) Freeze-dried injection preparation

Human EGF and human TGF$_\beta$ were dissolved in pyrogen-free 1/15M sodium phosphate buffer containing 0.001 w/v% of polyoxyethylene sorbitane fatty acid ester (Polysorbate 80) to give a final concentrations of 20 μg/ml and 10 mg/ml, respectively. With the pH being adjusted to 7.4, sodium chloride with the final concentration of 75 mM was added. This solution was subjected to filtration for removal of microorganisms in the same manner as in Example 1, and from the resultant solution, freeze-dried injection preparation was prepared in the same manner as in Example 3.

(Example 67) Freeze-dried injection preparation

Human IGF-II was dissolved in pyrogen-free 1/15M sodium phosphate buffer containing 0.1 w/v% gelatin to give a final concentration of 10 μg/ml. With the pH being adjusted to 7.7, sodium chloride with the final concentration of 73.6 mM was added. This solution was subjected to filtration for removal of mircoorganisms in the same manner as in Example 1, and from the resultant solution, a freeze-dried injection preparation was prepared in the same manner as in Example 3.

(Example 68) Freeze-dried injection preparation

Human IGF-II was dissolved in pyrogen-free 1/15M sodium phosphate buffer containing 0.001 w/v% polyoxyethylene sorbitan fatty acid ester (Polysorbate 80) to give a final concentration of 10 μg/ml. With the pH being adjusted to 7.7, sodium chloride with the final concentration of 73.6 mM was added. This solution was subjected to filtration for removal of microorganisms in the same manner as in Example 1, and from the resultant solution, a freeze-dried injection preparation was prepared in the same manner as in Example 3.

What is claimed is:

1. An antitumor composition, comprising (a) a compound having antitumor action which is at least one compound selected from the group consisting of alkylating agents, antimetabolites, antibiotics and platinum complexes, and (b) a growth factor which is at least one compound selected from the group consisting of compounds of the epidermal growth factor family and compounds of the platelet-derived growth factor family;
   wherein said alkylating agents are selected from the group consisting of chloromethyne analogues, nitrogen mustard analogues, ethyleneimino analogues, alkylsulfonic acid analogues, nitrosourea analogues, and epoxide analogues;
   wherein said antimetabolites are selected from the group consisting of folic acid antagonist analogues, purine antagonist analogues, pyridine antagonist analogues, Tegafur, and uracil formulated into Tegafur;

wherein said antibiotics are selected from the group consisting of actinomycin analogues, azaserine, DON, sarkomycin, carzinophilin, mitomycin analogues, chromomycin $A_3$ analogues, bleomycin, peplomycin, daunorubicin, adriamycin, and aclarubicin; and wherein said platinum complexes are selected from the group consisting of cisplatin, carboplatin, ipuloplatin.

2. An antitumore composition according to claim 1, wherein the compound having antitumor action, component (a), is an alkylating agent, and the growth factor or the growth factor equivalent, component (b), is a compound belonging to the epidermal growth factor family, a peptide corresponding to a part of its constituent or a derivative of these.

3. An antitumor composition according to claim 1, wherein the alkylating agent is cyclophosphamide or a derivative thereof or a salt of these, and the compound belonging to the epidermal cell growth factor family, the peptide growth corresponding to a part of its constituent and the derivative of these is at least one compound selected from the group consisting of human epidermal growth factor (hereinafter written as hEGF), the derivative of human epidermal growth factor in which methionine which is the 21st amino acid from the N-terminal of the human epidermal growth factor is converted to leucine (hereinafter written as [Leu$^{21}$]-hEGF), the derivative of human epidermal growth factor in which two amino acids from the C-terminal (leucine and alginine) of the human epidermal growth factor are lacking (hereinafter written as hEGF-II), transforming growth factor $\alpha$ (hereinafter written as TGF$_\alpha$), and transforming growth factor $\beta$ (hereinafter written as TGF$_\beta$).

4. An antitumor agent according to claim 1, wherein the alkylating agent is cyclophosphamide or its derivative or a salt of these, and the compound belonging to the epidermal growth factor family, or the peptide corresponding to a part of its constituent or the derivative of these is hEGF.

5. An antitumor agent according to claim 1, wherein the alkylating agent is cyclophosphamide or its derivative or a salt of these, and the compound belonging to the epidermal growth factor family, the peptide corresponding to a part of its constituent or the derivative of these is [Leu$^{21}$]-hEGF.

6. An antitumor agent according to claim 1, wherein the alkylating agent is cyclophosphamide or its derivative or a salt of these, and the compound belonging to the epidermal growth factor family, the peptide corresponding to a part of its constituent or the derivative of these is hEGF-II.

7. An antitumor agent according to claim 1, wherein the alkylating agent is cyclophosphamide or its derivative or a salt of these, and the compound belonging to the epidermal growth factor family, the peptide corresponding to a part of its constituent or the derivative of these is TGF$_\alpha$.

8. An antitumor agent according to claim 1, wherein the alkylating agent is cyclophosphamide or its derivative or a salt of these, and the compound belonging to the epidermal growth factor family, the peptide corresponding to a part of its constituent or the derivative of these is a mixture of hEGF and TGF$_\beta$.

9. An antitumor agent according to claim 3, wherein cyclophosphamide or its derivative is cyclophosphamide.

10. An antitumor agent according to claim 1, wherein the compound having antitumor action, component (a), is an antimetabolite, and the growth factor or the growth factor equivalent, component (b), is a compound belonging to the epidermal growth factor family, a peptide corresponding to a part of its constituent or a derivative of these.

11. An antitumor agent according to claim 1, wherein the antimetabolite is at least one compound or a mixture selected from 5-fluorouracil, or its derivative or salts of these, Tegafur or its derivative or salts of these, or a mixture of Tegafur or its derivative or salts of these with uracil, and the compound belonging to the epidermal growth factor family, the growth factor equivalent is at least one compound selected from hEGF, [Leu$^{21}$]-hEGF, hEGF-II, TGF$_\alpha$ and TGF$_\beta$.

12. An antitumor agent according to claim 1, wherein the antimetabolite is 5-fluorouracil or its derivative or a salt of these, and the compound belonging to the epidermal growth factor family, the growth factor equivalent to a part of its constituent or the derivative of these is hEGF.

13. An antitumor agent according to claim 1, wherein the antimetabolite is 5-fluorouracil or its derivative or a salt of these, and the compound belonging to the epidermal growth factor family, the growth factor equivalent is [Leu$^{21}$]-hEGF.

14. An antitumor agent according to claim 1, wherein the antimetabolite is 5-fluorouracil or its derivative or a salt of these, and the compound belonging to the epidermal growth factor family, the peptide corresponding to a part of its constituent or the derivative of these is hEGF-II.

15. An antitumor agent according to claim 1, wherein the antimetabolite is 5-fluorouracil or its derivative or a salt of these, and the compound belonging to the epidermal growth factor family, the peptide corresponding to a part of its constituent or the derivative of these is TGF$_\alpha$.

16. An antitumor agent according to claim 1, wherein the antimetabolite is 5-fluorouracil or its derivative or a salt of these, and the compound belonging to the epidermal growth factor family, the peptide corresponding to a part of its constituent or the derivative of these is a mixture of hEGF and TGF$_\beta$.

17. An antitumor agent according to claim 11, wherein 5-fluorouracil or its derivative is 5-fluorouracil.

18. An antitumor agent according to claim 1, wherein the antimetabolite is Tegafur or its derivative or a salt of these, and the compound belonging to the epidermal growth factor family, the peptide corresponding to a part of its constituent or the derivative of these is hEGF.

19. An antitumor agent according to claim 1, wherein the antimetabolite is Tegafur or its derivative or a salt of these, and the compound belonging to the epidermal growth factor family, the peptide corresponding to a part of its constituent or the derivative of these is [Leu$^{21}$]-hEGF.

20. An antitumor agent according to claim 1, wherein the antimetabolite is Tegafur or its derivative or a salt of these, and the compound belonging to the epidermal growth factor family, the peptide corresponding to a part of its constituent or the derivative of these is hEGF-II.

21. An antitumor agent according to claim 1, wherein the antimetabolite is Tegafur or its derivative or a salt of these, and the compound belonging to the epidermal growth factor family, the peptide corresponding to a part of its constituent or the derivative of these is TGF$_\alpha$.

22. An antitumor agent according to claim 1, wherein the antimetabolite is Tegafur or its derivative or a salt of these, and the compound belonging to the epidermal growth factor family, the peptide corresponding to a part of its constituent or the derivative of these is a mixture of hEGF and TFG.

23. An antitumor agent according to claim 1, wherein the antimetabolite is a mixture of Tegafur or its derivative or a salt of these and uracil, and the compound belonging to the epidermal growth factor family, the peptide corresponding to a part of its constituent or the derivative of these is hEGF.

24. An antitumor agent according to claim 1, wherein the antimetabolite is a mixture of Tegafur or its derivative of a salt of these and uracil, and the compound belonging to the epidermal growth factor family, the peptide corresponding to a part of its constituent or the derivative of these is [Leu$^{21}$]-hEGF.

25. An antitumor agent according to claim 1, wherein the antimetabolite is a mixture of Tegafur or its derivative of a salt of these and uracil, and the compound belonging to the epidermal growth factor family, the peptide corresponding to a part of its constituent or the derivative of these is hEGF-II.

26. An antitumor agent according to claim 1, wherein the antimetabolite is a mixture of Tegafur or its derivative or a salt of these and uracil, and the compound belonging to the epidermal growth factor family, the peptide corresponding to a part of its constituent or the derivative of these is TGF$_\alpha$.

27. An antitumor agent according to claim 1, wherein the antimetabolite is a mixture of Tegafur or its derivative or a salt of these and uracil, and the compound belonging to the epidermal growth factor family, the peptide corresponding to a part of its constituent or the derivative of these is a mixture of hEGF and TGF$_\beta$.

28. An antitumor agent according to claim 19, wherein Tegafur or its derivative is Tegafur.

29. An antitumor agent according to claim 1, wherein the compound having antitumor action, component (a), is an antimetabolite, and the growth factor or the growth factor equivalent, component (b), is a compound belonging to the platelet derived growth factor family, a peptide corresponding to a part of its constituent or a derivative of these.

30. An antitumor agent according to claim 1, wherein the antimetabolite is at least one compound or a mixture selected from 5-fluorouracil, or its derivative or salts of these, Tegafur or its derivative or salts of these, or a mixture of Tegafur or its derivative or salts of these with uracil, and the compound belonging to the platelet-derived growth factor family, the peptide corresponding to a part of its constituent or the derivative of these is fibroblast growth factor (hereinafter written a FGF).

31. An antitumor agent according to claim 1, wherein the antimetabolite is 5-fluorouracil, or its derivative or a salt of these, and the compound belonging to the platelet-derived growth factor family, the peptide corresponding to a part of its constituent or the derivative of these is FGF.

32. An antitumor agent according to claim 30, wherein 5-fluorouracil or its derivatives is 5-fluorouracil.

33. An antitumor agent according to claim 1, wherein the antimetabolite is Tegafur, or its derivative or a salt of these, and the compound belonging to the platelet-derived growth factor family, the peptide corresponding to a part of its constituent or the derivative of these is FGF.

34. An antitumor agent according to claim 1, wherein the antimetabolites is a mixture of Tegafur, or its derivative or a salt of these and uracil, and the compound belonging to the platelet-derived growth factor family, the peptide corresponding to a part of its constituent or the derivative of these is FGF.

35. An antitumor agent according to claim 33, wherein Tegafur or its derivatives is Tegafur.

36. An antitumor agent according to claim 1, wherein the compound having antitumor action, component (a), is an antitumor antibiotic, and the growth factor or the growth factor equivalent, component (b), is a compound belonging to the epidermal growth factor family.

37. An antitumor agent according to claim 1, wherein the antibiotic is at least one compound selected from mitomycin, derivatives thereof or salts thereof, or adriamycin, or derivative thereof or salts thereof, and the compound belonging to the epidermal cell growth family, the peptide corresponding to a part of its constituent and the derivative of these is at least one compound selected from hEGF, hEGF-II and [Leu$^{21}$]-hEGF.

38. An antitumor agent according to claim 1, wherein the antibiotic is mitomycin, a derivative thereof or a salt of these, and the compound belonging to the epidermal growth factor family, the peptide corresponding to a part of its constituent, or the derivative of these is hEGF.

39. An antitumor agent according to claim 1, wherein the antibiotic is mitomycin, a derivative thereof or a salt of these, and the compound belonging to the epidermal growth factor family, the peptide corresponding to a part of its constituent, or the derivative of these is hEGF-II.

40. An antitumor agent according to claim 1, wherein the antibiotic is mitomycin, a derivative thereof or a salt of these, and the compound belonging to the epidermal growth factor family, the peptide corresponding to a part of its constituent, or the derivative of these is [Leu$^{21}$]-hEGF.

41. An antitumor agent according to claim 37, wherein mitomycin or its derivative is mitomycin C.

42. An antitumor agent according to claim 1, wherein the antibiotic is adriamycin, a derivative thereof or a salt of these, and the compound belonging to the epidermal growth factor family, the peptide corresponding to a part of its constituent, or the derivative of these is hEGF.

43. An antitumor agent according to claim 1, wherein the antibiotic is adriamycin, a derivative thereof or a salt of these, and the compound belonging to the epidermal growth factor family, the peptide corresponding to a part of its constituent, or the derivative of these is hEGF-II.

44. An antitumor agent according to claim 1, wherein the antibiotic is adriamycin, a derivative thereof or a salt of these, and the compound belonging to the epidermal growth factor family, the peptide corresponding to a part of its constituent, or the derivative of these is [Leu$^{21}$]-hEGF.

45. An antitumor agent according to claim 42, wherein adriamycin or its derivative is adriamycin.

46. An antitumor agent according to claim 39, wherein adriamycin, or its derivative is adriamycin.

47. An antitumor agent according to claim 1, wherein the compound having antitumor action, component (a), is a platinum complex, and the growth factor or the growth factor equivalent, component (b), is a compound belonging to the epidermal cell growth factor family.

48. An antitumor agent according to claim 1, wherein the compound having antitumor action is one member selected from the group consisting of cisplatin, derivatives thereof and salts thereof, adriamycin, derivatives thereof and salts thereof, and the compound belonging to the epidermal growth family, the peptide corresponding to part of its constituent and the derivative of these is at least one compound selected from hEGF, hEGF-II and [Leu$^{21}$]-hEGF.

49. An antitumor agent according to claim 1, wherein the platinum complex is cisplatin, a derivative thereof or a salt of these, and the compound belonging to the epidermal growth factor family, the peptide corresponding to a part of its constituent, or the derivative of these is hEGF.

50. An antitumor agent according to claim 1, wherein the platinum complex is cisplatin, a derivative thereof or a salt of these, and the compound belonging to the epidermal growth factor family, the peptide corresponding to a part of its constituent, or the derivative of these is hEGF-II.

51. An antitumor agent according to claim 1, wherein the platinum complex is cisplatin, a derivative thereof or a salt of these, and the compound belonging to the epidermal growth factor family, the peptide corresponding to a part of its constituent, or the derivative of these is [Leu$^{21}$]-hEGF.

52. An antitumor agent according to claim 48, wherein cisplatin or its derivative is cisplatin.

53. A method of controlling antitumor action in chemotherapy, radiation therapy or thermotherapy in which antitumor treatment is practiced, which method comprises administering to a patient under said treatment, during or after the application to the patient of an antitumor chemical which is at least one compound selected from the group consisting of alkylating agents, antimetabolites, antibiotics and platinum complexes, irradiation or heat, an antitumor controlling composition, comprising a growth factor which is at least one compound selected from the group consisting of compounds of the epidermal growth factor family and compounds of the platelet-derived growth factor family;

wherein said alkylating agents are selected from the group consisting of chloromethyne analogues, nitrogen mustard analogues, ethyleneimino analogues, alkylsulfonic acid analogues, nitrosourea analogues, and epoxide analogues;

wherein said antimetabolites are selected from the group consisting of folic acid antagonist analogues, purine antagonist analogues, pyridine antagonist analogues, Tegafur, and uracil formulated into Tegafur;

wherein said antibiotics are selected from the group consisting of actinomycin analogues, azaserine, DON, sarkomycin, carzinophilin, mitomycin analogues, chromomycin A$_3$ analogues, bleomycin, peplomycin, daunorubicin, adriamycin, and aclarubicin; and wherein said platinum complexes are selected from the group consisting of cisplatin, carboplatin, ipuloplatin.

54. A method of controlling antitumor action according to claim 53, wherein the growth factor, the peptide corresponding to a part of its constituent and the derivative of these is a compound belonging to the epidermal growth factor family, a peptide corresponding to a part of its constituent or a derivative of these.

55. A method of controlling antitumor action according to claim 54, wherein the compound belonging to the epidermal growth factor family, the peptide corresponding to a part of its constituent and the derivative of these is at least one compound selected from the group consisting of human epidermal growth factor (hereinafter written as hEGF), the derivative of human epidermal growth factor in which methionine which is the 21st amino acid from the N-terminal of human epidermal growth factor is converted to leucine (hereinafter written as [Leu$^{21}$]-hEGF), the derivative of human epidermal growth factor in which two amino acids from the C-terminal (leucine and alginine) of the human epidermal growth factor are lacking (hereinafter written as hEGF-II), transforming growth factor α (hereinafter written as TGSF$_\alpha$), and transforming growth factor β (hereinafter written as TGF$_\beta$).

56. A method of controlling antitumor action according to claim 55, wherein the compound belonging to the epidermal growth factor family, the peptide corresponding to a part of its constituent or the derivative of these is hEGF.

57. A method of controlling antitumor action according to claim 55, wherein the compound belonging to the epidermal growth factor family, the peptide corresponding to a part of its constituent or the derivative of these is [Leu$^{21}$]-hEGF.

58. A method of controlling antitumor action according to claim 55, wherein the compound belonging to the epidermal growth factor family, the peptide corresponding to a part of its constituent or the derivative of these is hEGF-II.

59. A method of controlling antitumor action according to claim 53, wherein the compound belonging to the epidermal growth factor family, the peptide corresponding to a part of its constituent or the derivative of these is TGF$_\alpha$.

60. A method of controlling antitumor action according to claim 55, wherein the compound belonging to the epidermal growth factor family, the peptide corresponding to a part of its constituent or the derivative of these is a mixture of hEGF and TGF$_\beta$.

61. A method for controlling antitumor action according to claim 53, wherein the growth factor, or the growth factor equivalent is a compound belonging to the platelet-derived growth factor family, a peptide corresponding to a part of its constituent or a derivative of these.

62. A method for controlling antitumor action according to claim 61, wherein the compound belonging to the platelet-derived growth factor family, the peptide corresponding to a part of its constituent or the derivative of these is fibroblast cell growth factor (hereinafter written as FGF).

* * * * *